United States Patent
Ishii

(10) Patent No.: US 8,903,042 B2
(45) Date of Patent: Dec. 2, 2014

(54) RADIOGRAPHIC SYSTEM AND RADIOGRAPHIC IMAGE GENERATING METHOD

(71) Applicant: FUJIFILM Corporation, Tokyo (JP)

(72) Inventor: Hiroyasu Ishii, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/871,392

(22) Filed: Apr. 26, 2013

(65) Prior Publication Data

US 2013/0308750 A1 Nov. 21, 2013

Related U.S. Application Data

(63) Continuation of application No. PCT/JP2011/074552, filed on Oct. 25, 2011.

(30) Foreign Application Priority Data

Oct. 27, 2010 (JP) .................................. 2010-241099

(51) Int. Cl.
*A61B 6/00* (2006.01)
*G01N 23/04* (2006.01)

(52) U.S. Cl.
CPC .............. *A61B 6/4291* (2013.01); *A61B 6/4452* (2013.01); *A61B 6/4464* (2013.01); *A61B 6/484* (2013.01); *A61B 6/4233* (2013.01); *G01N 23/04* (2013.01); *A61B 6/502* (2013.01)
USPC .......................................... 378/62; 378/207

(58) Field of Classification Search
CPC ...... A61B 6/484; A61B 6/4291; A61B 6/502; A61B 6/5258; A61B 6/5264
USPC ....................................... 378/36, 62, 82, 207
See application file for complete search history.

(56) References Cited

U.S. PATENT DOCUMENTS

| | | | |
|---|---|---|---|
| 2007/0189449 A1 | 8/2007 | Baumann et al. | |
| 2010/0119041 A1 | 5/2010 | Ohara | |
| 2011/0235780 A1* | 9/2011 | Tada | 378/62 |
| 2012/0140885 A1* | 6/2012 | Iwakiri et al. | 378/62 |
| 2012/0183123 A1* | 7/2012 | Tada | 378/62 |
| 2012/0275564 A1* | 11/2012 | Hashimoto | 378/62 |

(Continued)

FOREIGN PATENT DOCUMENTS

| | | |
|---|---|---|
| JP | 2009-525084 A | 7/2009 |
| WO | WO 2008/102685 A1 | 8/2008 |

OTHER PUBLICATIONS

Bech et al., "Hard X-ray phase-contrast imaging with the Compact Light Source based on inverse Compton X-rays", Journal of Synchrotron Radiation, vol. 16, Part 1, pp. 43-47, (Jan. 1, 2009).*

(Continued)

*Primary Examiner* — Glen Kao
(74) *Attorney, Agent, or Firm* — Jean C. Edwards, Esq.; Edwards Neils PLLC

(57) ABSTRACT

In a radiographic system and a radiographic image generating method that generate a phase contrast image and an absorption image of an subject, the absorption image in which density irregularity is removed or reduced is generated on the basis of a plurality of pieces of image data obtained for generating the phase contrast image.

10 Claims, 16 Drawing Sheets

(56) References Cited

U.S. PATENT DOCUMENTS

| | | | |
|---|---|---|---|
| 2013/0083893 A1* | 4/2013 | Ishii | 378/62 |
| 2013/0201198 A1* | 8/2013 | Nagatsuka et al. | 345/581 |
| 2014/0044234 A1* | 2/2014 | Hashimoto et al. | 378/62 |

OTHER PUBLICATIONS

Weitkamp et al., "Hard X-ray phase imaging and tomography with a grating interferometer", Developments in X-Ray Tomography IV, Proceedings of SPIE, vol. 5535, pp. 137-142, (Oct. 26, 2004).*

Katsuyuki Kawabata, Imaging Application of Visibility Lowering in X-ray Talbot Interferometer, (online) Tokyo University Academic Organization Repository, Mar. 24, 2010.

PCT/ISA/237 form from prior International Application PCT/JP2011/074552.

Extended European Search Report issued by the EPO on Feb. 17, 2014 in connection with corresponding European Patent Application 11836273.0.

Bech, et al., "Hard X-ray Phase-Contrast Imaging with the Compact Light Source Based on Inverse Compton X-rays," Journal of Synchrotron Radiation, Nov. 27, 2008, pp. 43-47.

Weitkamp, et al., "Hard X-ray Phase Imaging and Tomography with a Grating Interferometer," Proceedings of Intl. Society for Optical Engineering, Oct. 1, 2004, pp. 137-142.

* cited by examiner

RADIOGRAPHIC SYSTEM AND RADIOGRAPHIC IMAGE GENERATING METHOD

CROSS REFERENCE TO RELATED APPLICATION

This is a continuation of International Application No. PCT/JP2011/074552 filed on Oct. 25, 2011, and claims priority from Japanese Patent Application No. 2010-241099, filed on Oct. 27, 2010, the entire disclosures of which are incorporated herein by reference.

TECHNICAL FIELD

The present invention relates to a radiographic system and a radiographic image generating method.

BACKGROUND ART

Since X-ray attenuates depending on an atomic number of an element configuring a material and a density and a thickness of the material, it is used as a probe for seeing through an inside of a subject. An imaging using the X-ray is widely spread in fields of medical diagnosis, nondestructive inspection and the like.

In a conventional X-ray imaging system, a subject is arranged between an X-ray source that irradiates the X-ray and an X-ray image detector that detects an X-ray image, and a transmission image of the subject is captured. In this case, the X-ray irradiated from the X-ray source toward the X-ray image detector is subject to the quantity attenuation (absorption) depending on differences of the material properties (for example, atomic numbers, densities and thickness) existing on a path to the X-ray image detector and is then incident onto the X-ray image detector. As a result, an X-ray transmission image of the subject is detected and captured by the X-ray image detector to obtain an image (hereinafter, referred to as an absorption image) based on an intensity change of the X-ray by the subject. As the X-ray image detector, a flat panel detector (FPD) that uses a semiconductor circuit is widely used, in addition to a combination of an X-ray intensifying screen and a film and a photostimulable phosphor (accumulative phosphor).

However, the smaller the atomic number of the element configuring material, the X-ray absorption ability is reduced. Accordingly, for the soft biological tissue or soft material, a difference of the X-ray absorption abilities is small and thus it is not possible to acquire an enough contrast of an image. For example, the cartilaginous part and joint fluid configuring an articulation of the body are mostly comprised of water. Thus, since a difference of the X-ray absorption amounts thereof is small, it is difficult to obtain the contrast of an image.

Regarding the above problems, instead of the intensity change of the X-ray by the subject, a research on an X-ray phase imaging of obtaining an image (hereinafter, referred to as a phase contrast image) based on a phase change (refraction angle change) of the X-ray by the subject has been actively carried out in recent years. In general, it has been known that when the X-ray is incident onto an object, the phase of the X-ray, rather than the intensity of the X-ray, shows the higher interaction. Accordingly, in the X-ray phase imaging of using the phase difference, it is possible to obtain a high contrast image even for a weak absorption material having a low X-ray absorption ability. As the X-ray phase imaging, an X-ray imaging system has been recently suggested which uses an X-ray Talbot interferometer having two transmission diffraction gratings (phase type grating and absorption type grating) and an X-ray image detector (for example, refer to Patent Literature 1).

The X-ray Talbot interferometer includes a first diffraction grating (phase type grating or absorption type grating) that is arranged at a rear side of a subject, a second diffraction grating (absorption type grating) that is arranged downstream at a specific distance (Talbot interference distance) determined by a grating pitch of the first diffraction grating and an X-ray wavelength, and an X-ray image detector that is arranged at a rear side of the second diffraction grating. The Talbot interference distance is a distance in which the X-ray having passed through the first diffraction grating forms a self-image by the Talbot interference effect. The self-image is modulated by the interaction (phase change) of the subject, which is arranged between the X-ray source and the first diffraction grating, and the X-ray.

In the X-ray Talbot interferometer, moiré fringes generated by superposition of the self-image of the first diffraction grating and the second diffraction grating are detected, and the phase information of the subject is acquired by analyzing a change of the moiré fringes by the subject. As an example of the method of analyzing moiré fringes, a fringe scanning method is proposed. According to the fringe scanning method, a plurality of imaging is performed while the second diffraction grating is translation-moved with respect to the first diffraction grating in a direction, which is substantially parallel with a plane of the first diffraction grating and is substantially perpendicular to a grating direction (strip band direction) of the first diffraction grating, with a scanning pitch that is obtained by equally partitioning the grating pitch. Then, an angle distribution (differential image of a phase shift) of the X-ray refracted at the subject is acquired from changes of signal values of respective pixels obtained in the X-ray image detector. Based on the acquired angle distribution, it is possible to obtain a phase contrast image of the subject.

CITATION LIST

Patent Literature

Patent Literature 1 JP-A-2009-525084

SUMMARY OF INVENTION

Technical Problem

According to X-ray phase imaging, it is possible to obtain a high contrast image of an object of weak X-ray absorption of which visualization is difficult so far, but in addition, if it is possible to refer to an absorption image corresponding to a phase contrast image, it may assist in radiographic image interpretation In the radiographic system disclosed in Patent Literature 1, a plurality of pieces of image data obtained for generating a phase contrast image is used, and signal values of pixels for each corresponding pixel group between the image data are added up or averaged for imaging, to generate an absorption image. Further, the phase contrast image and the absorption image are overlaid for display, and thus, respective portions that have not been independently expressed supplement each other. However, density irregularity due to first and second diffraction gratings is included in the image data obtained by a radiographic image detector, and thus, the density irregularity is also expressed as image contrast in the absorption image, which may obstruct radiographic image interpretation.

In order to solve the above problem, an object of the invention is to provide a radiographic system and a radiographic image generating method that generate a phase contrast image and an absorption image of a subject, in which the absorption image in which density irregularity is removed or reduced is generated on the basis of a plurality of pieces of image data obtained for generating the phase contrast image.

Solution to Problem (1) It is a radiographic system including: a first grating; a grating pattern that has a cycle substantially matched with a pattern cycle of a radiographic image formed by radiation that passes through the first grating and is located at a plurality of different relative positions with respect to the radiographic image; a radiographic image detector that detects the radiographic image masked by the grating pattern located at each relative position to obtain a plurality of pieces of image data; a phase contrast image generating unit that generates a phase contrast image on the basis of a plurality of pieces of subject image data obtained by the radiographic image detector when imaging is performed with a subject being placed, in an advancing direction of the radiation that passes through the first grating, in front of the first grating or between the first grating and the grating pattern; and an absorption image generating unit that generates an absorption image on the basis of the plurality of pieces of subject image data, in which the absorption image generating unit performs a shading correction for the absorption image.

(2) It is a radiographic image generating method using a first grating, a grating pattern that has a cycle substantially matched with a pattern cycle of a radiographic image formed by radiation that passes through the first grating and is located at a plurality of different relative positions with respect to the radiographic image, and a radiographic image detector that detects the radiographic image masked by the grating pattern located at each relative position to obtain a plurality of pieces of image data, the method including: performing imaging with a subject being placed, in an advancing direction of the radiation that passes through the first grating, in front of the first grating or between the first grating and the grating pattern to obtain a plurality of pieces of subject image data; generating a phase contrast image and an absorption image on the basis of the plurality of pieces of obtained subject image data; and performing a shading correction for the generated absorption image.

Advantageous Effects of Invention

According to the invention, since the absorption image is generated from the plurality of pieces of image data obtained for the image contrast image, it is possible to perform favorable overlaying of the phase contrast image and the absorption image without deviation of an imaging position during imaging of the absorption image, and to reduce the burden of the subject compared with a case where separate imaging is performed for the absorption image. Further, by performing the shading correction for the generated absorption image, it is possible to remove or reduce density irregularity due to the first grating and the grating pattern from the absorption image, and to improve the accuracy of diagnosis or inspection.

DESCRIPTION OF EMBODIMENTS

Figure 1:
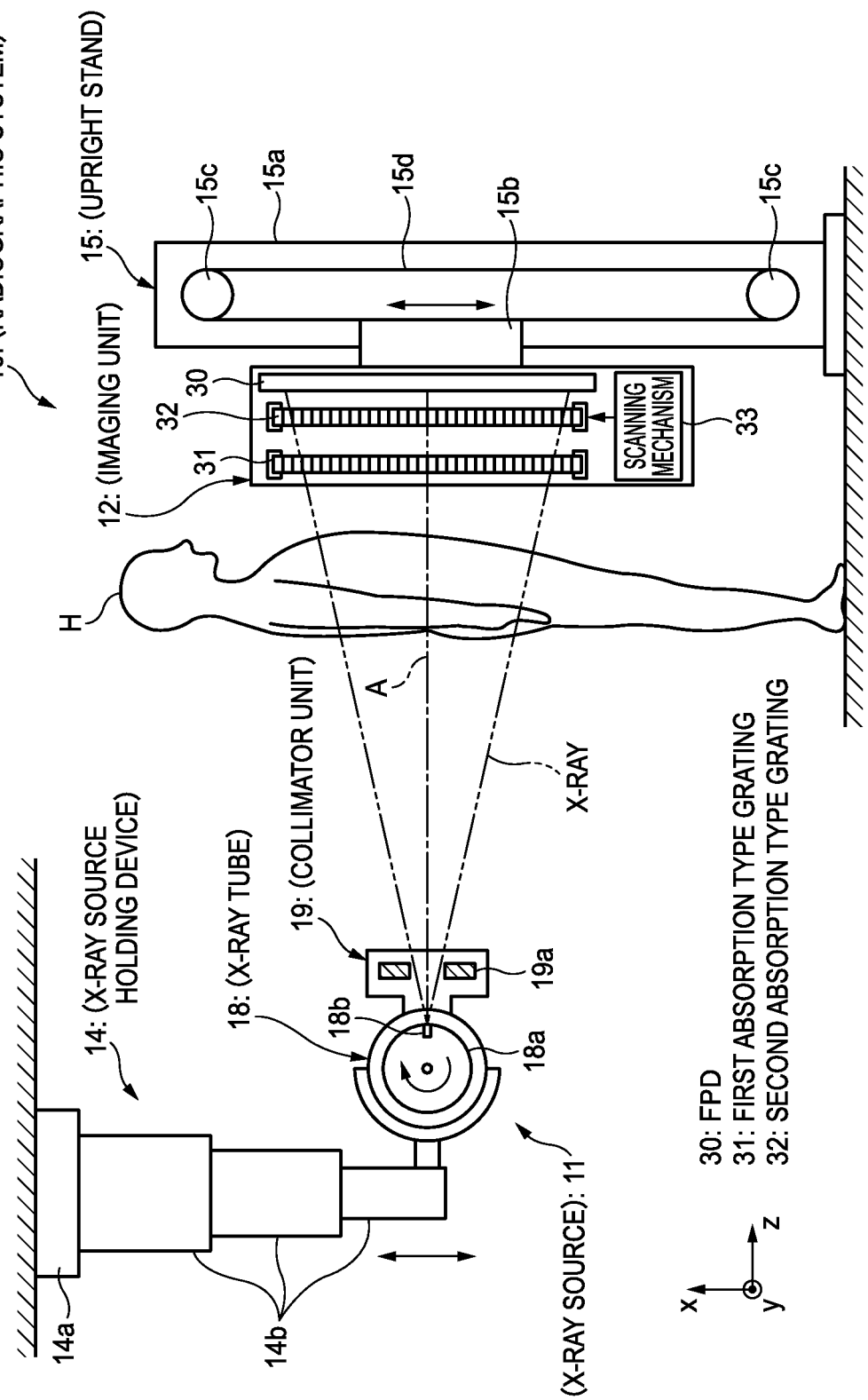
FIG. 1 is a diagram schematically illustrating a configuration of an example of a radiographic system according to an embodiment of the invention.
Figure 2:
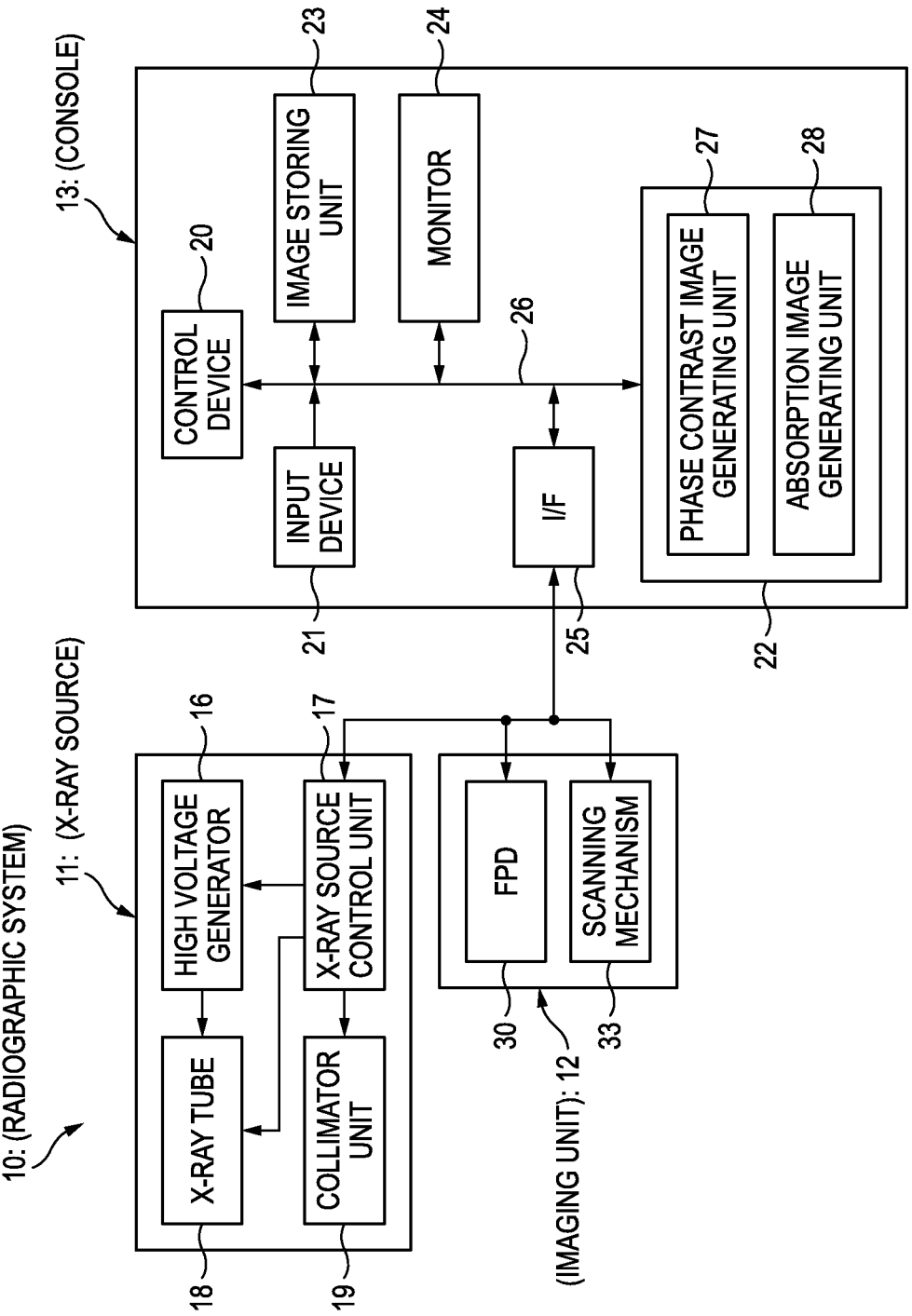
FIG. 2 is a control block diagram illustrating the radiographic system in FIG. 1.

FIG. 1 schematically illustrates a configuration of an example of radiographic system according to an embodiment of the invention and FIG. 2 illustrates a control block diagram illustrating the radiographic system in FIG. 1.

An X-ray imaging system 10 is an X-ray diagnosis apparatus that performs an imaging for a subject (patient) H while the patient stands, and includes an X-ray source 11 that X-radiates the subject H, an imaging unit 12 that is opposed to the X-ray source 11, detects the X-ray having penetrated the subject H from the X-ray source 11 and thus generates image data and a console 13 that controls an exposing operation of the X-ray source 11 and an imaging operation of the imaging unit 12 based on an operation of an operator, calculates the image data acquired by the imaging unit 12 and thus generates a phase contrast image and an absorption image.

The X-ray source 11 is held so that it can be moved in an upper-lower direction (x direction) by an X-ray source holding device 14 hanging from the ceiling. The imaging unit 12 is held that it can be moved in the upper-lower direction by an upright stand 15 mounted on the bottom.

The X-ray source 11 includes an X-ray tube 18 that generates the X-ray in response to a high voltage applied from a high voltage generator 16, based on control of an X-ray source control unit 17, and a collimator unit 19 having a moveable collimator 19a that limits an irradiation field so as to shield a part of the X-ray generated from the X-ray tube 18, which part does not contribute to an imaging of an inspection area of the subject H. The X-ray tube 18 is a rotary anode type that emits an electron beam from a filament (not shown) serving as an electron emission source (cathode) and collides the electron beam with a rotary anode 18a being rotating at predetermined speed, thereby generating the X-ray. A collision part of the electron beam of the rotary anode 18a is an X-ray focal point 18b.

The X-ray source holding device 14 includes a carriage unit 14a that is adapted to move in a horizontal direction (z direction) by a ceiling rail (not shown) mounted on the ceil and a plurality of strut units 14b that is connected in the upper-lower direction. The carriage unit 14a is provided with a motor (not shown) that expands and contracts the strut units 14b to change a position of the X-ray source 11 in the upper-lower direction.

The upright stand 15 includes a main body 15a that is mounted on the bottom and a holding unit 15b that holds the imaging unit 12 and is attached to the main body 15a so as to move in the upper-lower direction. The holding unit 15b is connected to an endless belt 15d that extends between two pulleys 15c spaced in the upper-lower direction, and is driven by a motor (not shown) that rotates the pulleys 15c. The driving of the motor is controlled by a control device 20 of the console 13 (which will be described later), based on a setting operation of the operator.

Also, the upright stand 15 is provided with a position sensor (not shown) such as potentiometer, which measures a moving amount of the pulleys 15c or endless belt 15d and thus detects a position of the imaging unit 12 in the upper-lower direction. The detected value of the position sensor is supplied to the X-ray source holding device 14 through a cable and the like. The X-ray source holding device 14 expands and contracts the struts units 14b, based on the detected value, and thus moves the X-ray source 11 to follow the vertical moving of the imaging unit 12.

The console 13 is provided with the control device 20 that includes a CPU, a ROM, a RAM and the like. The control device 20 is connected with an input device 21 with which the operator inputs an imaging instruction and an instruction content thereof, a calculation processing unit 22 that calculates the image data acquired by the imaging unit 12 and thus generates an X-ray image, a storage unit 23 that stores the X-ray image, a monitor 24 that displays the X-ray image and the like and an interface (I/F) 25 that is connected to the respective units of the X-ray imaging system 10, via a bus 26.

As the input device 21, a switch, a touch panel, a mouse, a keyboard and the like may be used, for example. By operating the input device 21, radiography conditions such as X-ray tube voltage, X-ray irradiation time and the like, an imaging timing and the like are input.

The calculation processing unit 22 includes a phase contrast image generating unit 27 that generates a phase contrast image on the basis of the image data obtained by the imaging unit 12, and an absorption image generating unit 28 that generates an absorption image. Processes in the respective generating units will be described in detail later.

The monitor 24 consists of a liquid crystal display and the like and displays letters such as radiography conditions and the X-ray image under control of the control device 20.

The imaging unit 12 has a flat panel detector (FPD) 30 that has a semiconductor circuit, and a first absorption type grating 31 and a second absorption type grating 32 that detect a phase change (angle change) of the X-ray by the subject H and perform a phase imaging.

The FPD 30 has a detection surface that is arranged to be orthogonal to the optical axis A of the X-ray irradiated from the X-ray source 11. As specifically described in the below, the first and second absorption type gratings 31, 32 are arranged between the FPD 30 and the X-ray source 11.

Also, the imaging unit 12 is provided with a scanning mechanism 33 that translation-moves the second absorption type grating 32 in the upper-lower (x direction) and thus changes a relative position relation of the second absorption type grating 32 to the first absorption type grating 31. The scanning mechanism 33 consists of an actuator such as piezoelectric device, for example.

Figure 3:
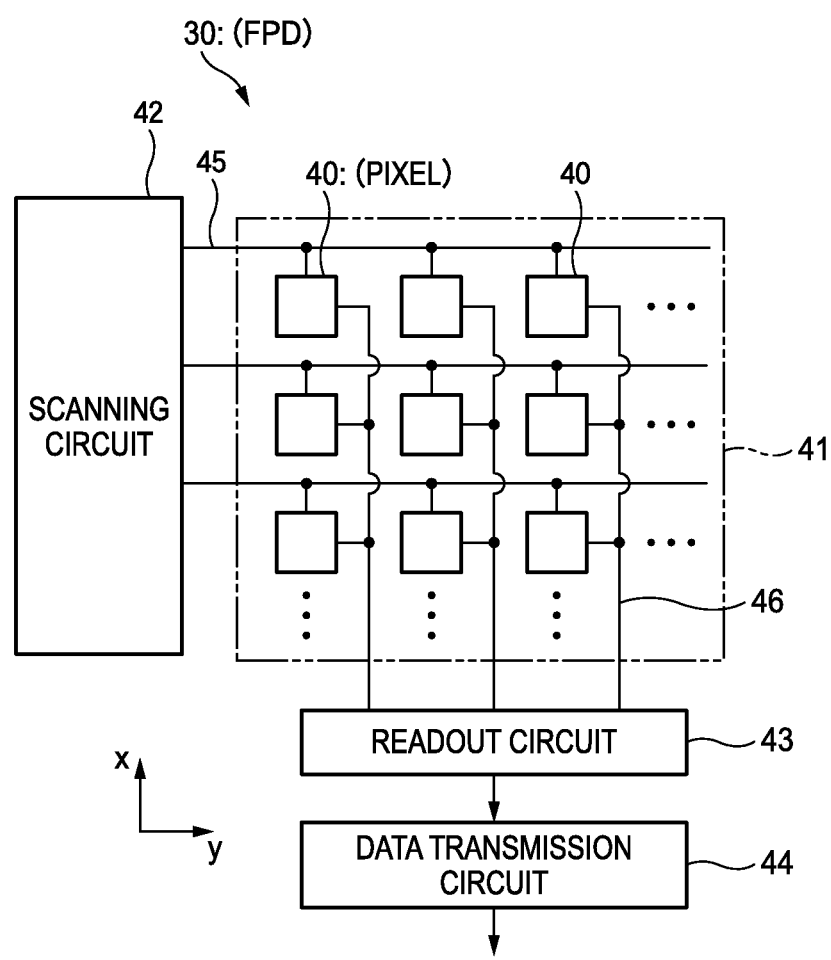
FIG. 3 is a diagram schematically illustrating a configuration of a radiographic image detector of the radiographic system in FIG. 1.

FIG. 3 illustrates a configuration of the radiological image detector of the radiographic system of FIG. 1.

The FPD 30 serving as the radiological image detector includes an image receiving unit 41 having a plurality of pixels 40 that converts and accumulates the X-ray into charges and is two-dimensionally arranged in the xy directions on an active matrix substrate, a scanning circuit 42 that controls a timing of reading out the charges from the image receiving unit 41, a readout circuit 43 that reads out the charges accumulated in the respective pixels 40 and converts and stores the charges into image data and a data transmission circuit 44 that transmits the image data to the calculation processing unit 22 through the I/F 25 of the console 13. Also, the scanning circuit 42 and the respective pixels 40 are connected by scanning lines 45 in each of rows and the readout circuit 43 and the respective pixels 40 are connected by signal lines 46 in each of columns.

Each pixel 40 can be configured as a direct conversion type element that directly converts the X-ray into charges with a conversion layer (not shown) made of amorphous selenium and the like and accumulates the converted charges in a capacitor (not shown) connected to a lower electrode of the conversion layer. Each pixel 40 is connected with a TFT (TFT: Thin Film Transistor) switch (not shown) and a gate electrode of the TFT switch is connected to the scanning line 45, a source electrode is connected to the capacitor and a drain electrode is connected to the signal line 46. When the TFT switch turns on by a driving pulse from the scanning circuit 42, the charges accumulated in the capacitor are read out to the signal line 46.

Meanwhile, each pixel 40 may be also configured as an indirect conversion type X-ray detection element that converts the X-ray into visible light with a scintillator (not shown) made of gadolinium oxysulfide ($Gd_2O_3$), cesium iodide (CsI) and the like and then converts and accumulates the converted visible light into charges with a photodiode (not shown). Also, the X-ray image detector is not limited to the FPD based on the TFT panel. For example, a variety of X-ray image detectors based on a solid imaging device such as CCD sensor, CMOS sensor and the like may be also used.

The readout circuit 43 includes an integral amplification circuit, an A/D converter, a correction circuit and an image memory, which are not shown. The integral amplification circuit integrates and converts the charges output from the respective pixels 40 through the signal lines 46 into voltage signals (image signals) and inputs the same into the A/D converter. The A/D converter converts the input image signals into digital image data and inputs the same to the correction circuit. The correction circuit performs an offset correction, a gain correction and a linearity correction for the image data and stores the image data after the corrections in the image memory. Meanwhile, the correction process of the correction circuit may include a correction of a pattern noise (for example, a leak signal of the TFT switch) depending on control conditions (driving frequency, readout period and the like) of the FPD 30, and the like.

Figure 4:
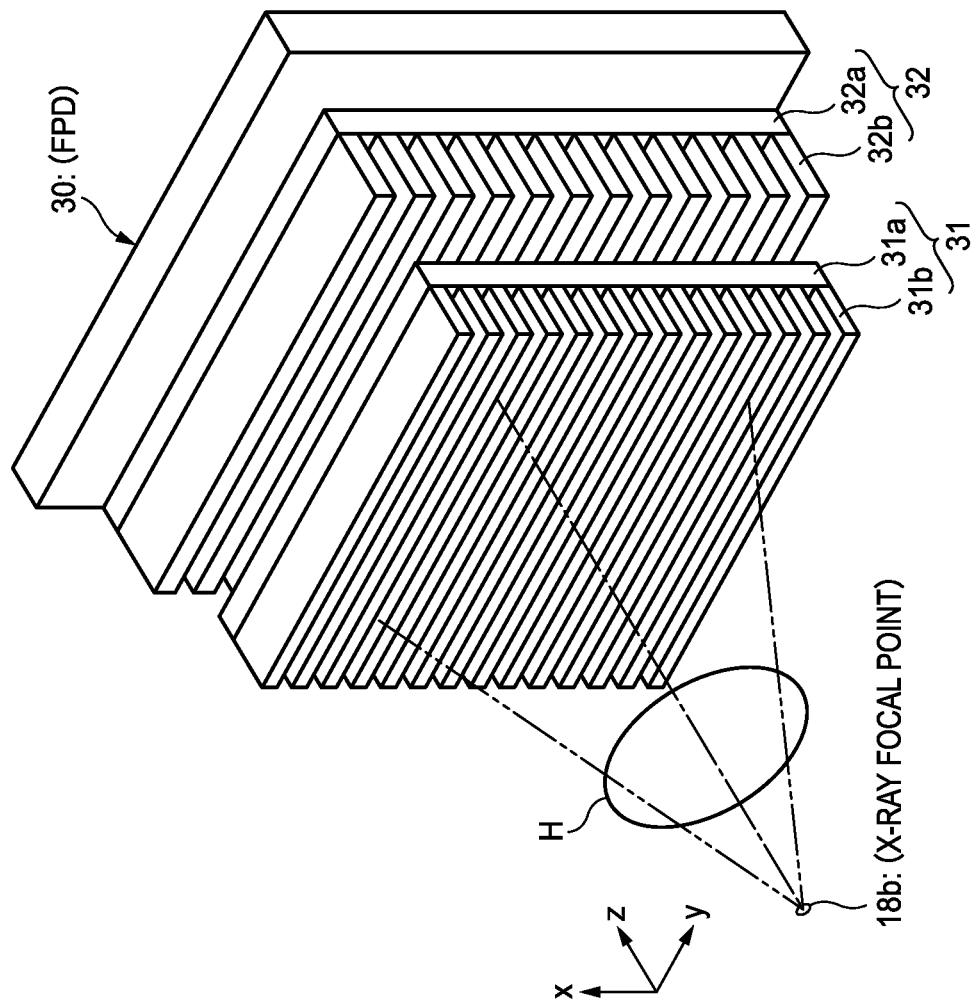
FIG. 4 is a perspective view illustrating an imaging unit of the radiographic system in FIG. 1.
Figure 5:
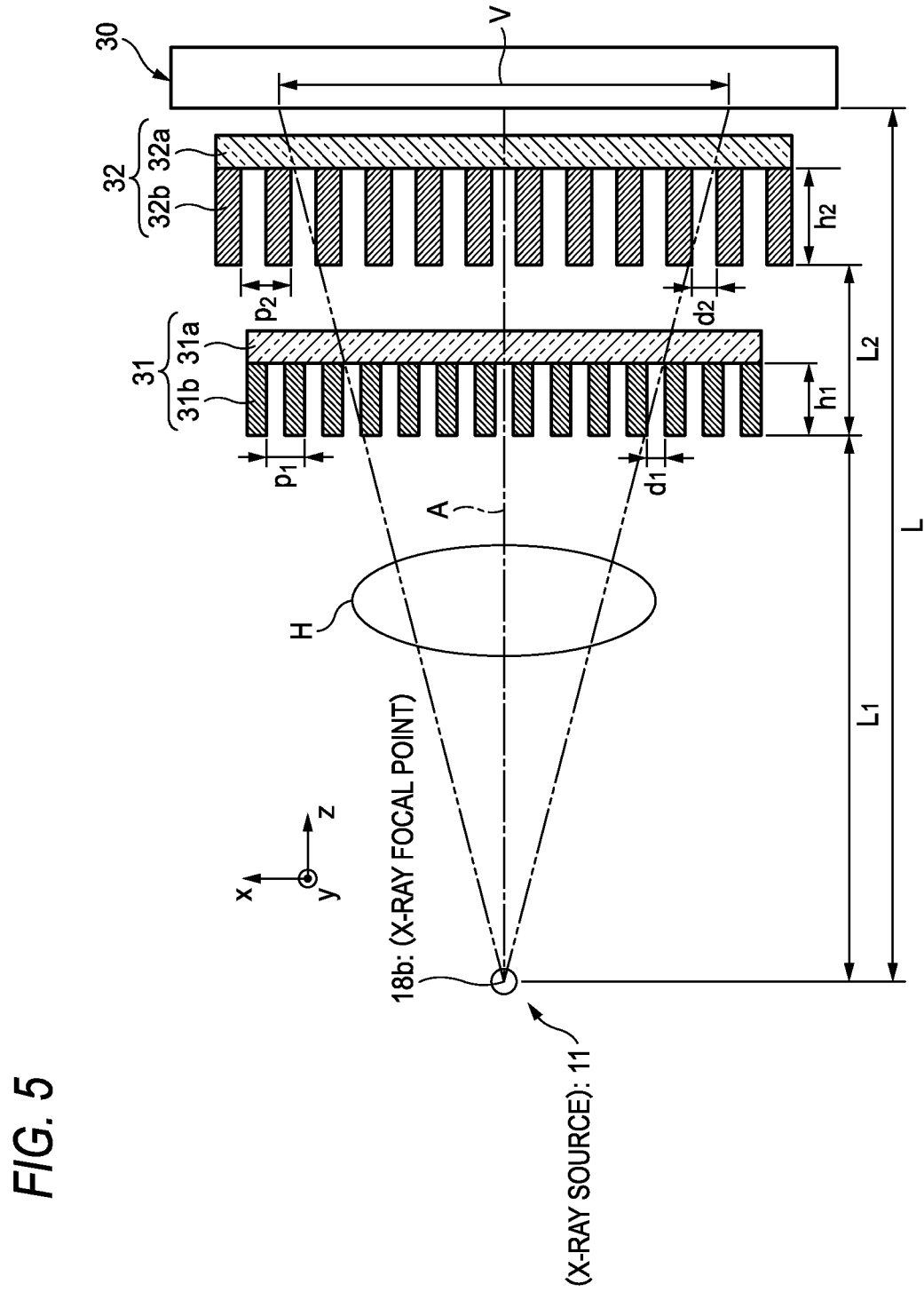
FIG. 5 is a side view illustrating the imaging unit of the radiographic system in FIG. 1.

FIGS. 4 and 5 illustrates the imaging unit of the radiographic system of FIG. 1.

The first absorption type grating 31 has a substrate 31a and a plurality of X-ray shield units 31b arranged on the substrate 31a. Likewise, the second absorption type grating 32 has a substrate 32a and a plurality of X-ray shield units 32b arranged on the substrate 32a. The substrates 31a, 32a are configured by radiolucent members through which the X-ray penetrates, such as glass.

The X-ray shield units 31b, 32b are configured by linear members extending in in-plane one direction (in the shown example, a y direction orthogonal to the x and z directions) orthogonal to the optical axis A of the X-ray irradiated from the X-ray source 11. As the materials of the respective X-ray shield units 31b, 32b, materials having excellent X-ray absorption ability are preferable. For example, the heavy metal such as gold, platinum and the like is preferable. The X-ray shield units 31b, 32b can be formed by the metal plating or deposition method.

The X-ray shielding units 31b are arranged in a plane perpendicular to the optical axis A of the X-ray at a predetermined interval d1 and a constant cycle p1 in the direction (x direction) perpendicular to the one direction. Similarly, the X-ray shielding units 32b are arranged in a plane perpendicular to the optical axis A of the X-ray at a predetermined interval d2 and a constant cycle p2 in the direction (x direction) perpendicular to the one direction. The first and second absorption type gratings 31 and 32 does not give a phase difference but give an intensity difference to the incident X-ray, and are thus referred to as amplitude gratings. Further, the slit portions (regions of the intervals d1 and d2) may not be an opening, and for example, the opening may be filled with a low X-ray absorber such as polymer or light metal.

The first and second absorption type gratings 31, 32 are adapted to geometrically project the X-ray having passed through the slits, regardless of the Talbot interference effect. Specifically, the intervals $d_1$, $d_2$ are set to be sufficiently larger than a peak wavelength of the X-ray irradiated from the X-ray source 11, so that most of the X-ray included in the irradiated X-ray is enabled to pass through the slits while keeping the linearity thereof, without being diffracted in the slits. For example, when the rotary anode 18a is made of tungsten and the tube voltage is 50 kV, the peak wavelength of the X-ray is about 0.4 Å. In this case, when the intervals $d_1$, $d_2$ are set to be about 1 to 10 μm, most of the X-ray is geometrically projected in the slits without being diffracted.

Since the X-ray irradiated from the X-ray source 11 is a conical beam having the X-ray focal point 18b as an emitting point, rather than a parallel beam, a projection image (hereinafter, referred to as G1 image), which has passed through the first absorption type grating 31 and is projected, is enlarged in proportion to a distance from the X-ray focal point 18b. The grating pitch $p_2$ of the second absorption type grating 32 are determined so that the slits substantially coincide with a periodic pattern of bright parts of the G1 image at the position of the second absorption type grating 32. That is, when a distance from the X-ray focal point 18b to the first absorption type grating 31 is $L_1$ and a distance from the first absorption type grating 31 to the second absorption type grating 32 is $L_2$, the grating pitch $p_2$ is determined to satisfy following equation (1).

[equation 1]
$$p_2 = \frac{L_1 + L_2}{L_1} p_1 \qquad (1)$$

In the Talbot interferometer, the distance $L_2$ from the first absorption type grating 31 to the second absorption type grating 32 is restrained with a Talbot interference distance that is determined by a grating pitch of a first diffraction grating and an X-ray wavelength. However, in the imaging unit 12 of the X-ray imaging system 10 of this illustrative embodiment, since the first absorption type grating 31 projects the incident X-ray without diffracting the same and the G1 image of the first absorption type grating 31 is similarly obtained at all positions of the rear of the first absorption type grating 31, it is possible to set the distance $L_2$ irrespective of the Talbot interference distance.

Although the imaging unit 12 does not configure the Talbot interferometer, as described above, a Talbot interference distance Z that is obtained if the first absorption type grating 31 diffracts the X-ray is expressed by a following equation (2) using the grating pitch $p_1$ of the first absorption type grating 31, the grating pitch $p_2$ of the second absorption type grating 32, the X-ray wavelength (peak wavelength) λ and a positive integer m.

[equation 2]
$$Z = m \frac{p_1 p_2}{\lambda} \qquad (2)$$

The equation (2) indicates a Talbot interference distance when the X-ray irradiated from the X-ray source 11 is a conical beam and is known by Atsushi Momose, et al. (Japanese Journal of Applied Physics, Vol. 47, No. 10, 2008, August, page 8077).

In the X-ray imaging system 10, the distance $L_2$ is set to be shorter than the minimum Talbot interference distance Z when m=1 so as to make the imaging unit 12 smaller. That is, the distance $L_2$ is set by a value within a range satisfying a following equation (4).

[equation 3]
$$L_2 < \frac{p_1 p_2}{\lambda} \qquad (3)$$

In addition, when the X-ray irradiated from the X-ray source 11 can be considered as a substantially parallel beam, the Talbot interference distance Z is expressed by a following equation (4) and the distance $L_2$ is set by a value within a range satisfying a following equation (5).

[equation 4]
$$Z = m \frac{p_1^2}{\lambda} \qquad (4)$$

[equation 5]
$$L_2 < \frac{p_1^2}{\lambda} \qquad (5)$$

In order to generate a period pattern image having high contrast, it is preferable that the X-ray shield units 31b, 32b perfectly shield (absorb) the X-ray. However, even when the materials (gold, platinum and the like) having excellent X-ray absorption ability are used, many X-rays penetrate the X-ray shield units without being absorbed. Accordingly, in order to improve the shield ability of X-ray, it is preferable to make thickness $h_1$, $h_2$ of the X-ray shield units 31*b*, 32*b* thicker as much as possible, respectively. For example, when the tube voltage of the X-ray tube 18 is 50 kV, it is preferable to shield 90% or more of the irradiated X-ray. In this case, the thickness $h_1$, $h_2$ are preferably 30 nm or larger, based on gold (Au).

In the meantime, when the thickness $h_1$, $h_2$ of the X-ray shield units 31*b*, 32*b* are excessively thickened, it is difficult for the obliquely incident X-ray to pass through the slits. Thereby, the so-called vignetting occurs, so that an effective field of view of the direction (x direction) orthogonal to the extending direction (strip band direction) of the X-ray shield units 31*b*, 32*b* is narrowed. Therefore, from a standpoint of securing the field of view, the upper limits of the thickness $h_1$, $h_2$ are defined. In order to secure a length V of the effective field of view in the x direction on the detection surface of the FPD 30, when a distance from the X-ray focal point 18*b* to the detection surface of the FPD 30 is L, the thickness $h_1$, $h_2$ are necessarily set to satisfy following equations (6) and (7), from a geometrical relation shown in FIG. 5.

[equation 6]

$$h_1 \leq \frac{L}{V/2} d_1 \quad (6)$$

[equation 7]

$$h_2 \leq \frac{L}{V/2} d_2 \quad (7)$$

For example, when $d_1$=2.5 μm, $d_2$=3.0 μm and L=2 m, assuming a typical imaging in a typical hospital, the thickness $h_1$ should be 100 μm or smaller and the thickness $h_2$ should be 120 nm or smaller so as to secure a length of 10 cm as the length V of the effective field of view in the x direction.

In the imaging unit 12 configured as described above, an intensity-modulated image is formed by the superimposition of the G1 image of the first absorption type grating 31 and the second absorption type grating 32 and is captured by the FPD 30. A pattern period $p_1'$ of the G1 image at the position of the second absorption type grating 32 and a substantial grating pitch $p_2'$ (substantial pitch after the manufacturing) of the second absorption type grating 32 are slightly different due to the manufacturing error or arrangement error. The arrangement error means that the substantial pitches of the first and second absorption type gratings 31, 32 in the x direction are changed as the inclination, rotation and the interval therebetween are relatively changed.

Due to the slight difference between the pattern period $p_1'$ of the G1 image and the grating pitch $p_2'$, the image contrast becomes a moiré fringe. A period T of the moiré fringe is expressed by a following equation (8).

[equation 8]

$$T = \frac{p1' \times p2'}{|p1' - p2'|} \quad (8)$$

When it is intended to detect the moiré fringe with the FPD 30, an arrangement pitch P of the pixels 40 in the x direction should satisfy at least a following equation (9) and preferably satisfy a following equation (10) (n: positive integer).

[equation 9]

$$p \neq nT \quad (9)$$

[equation 10]

$$P < T \quad (10)$$

The equation (9) means that the arrangement pitch P is not an integer multiple of the moiré period T. Even for a case of n≥2, it is possible to detect the moiré fringe in principle. The equation (10) means that the arrangement pitch P is set to be smaller than the moiré period T.

Since the arrangement pitch P of the pixels 40 of the FPD 30 are design-determined (in general, about 100 nm) and it is difficult to change the same, when it is intended to adjust a magnitude relation of the arrangement pitch P and the moiré period T, it is preferable to adjust the positions of the first and second absorption type gratings 31, 32 and to change at least one of the pattern period $p_1'$ of the G1 image and the grating pitch $p_2'$, thereby changing the moiré period T.

Figure 6A:
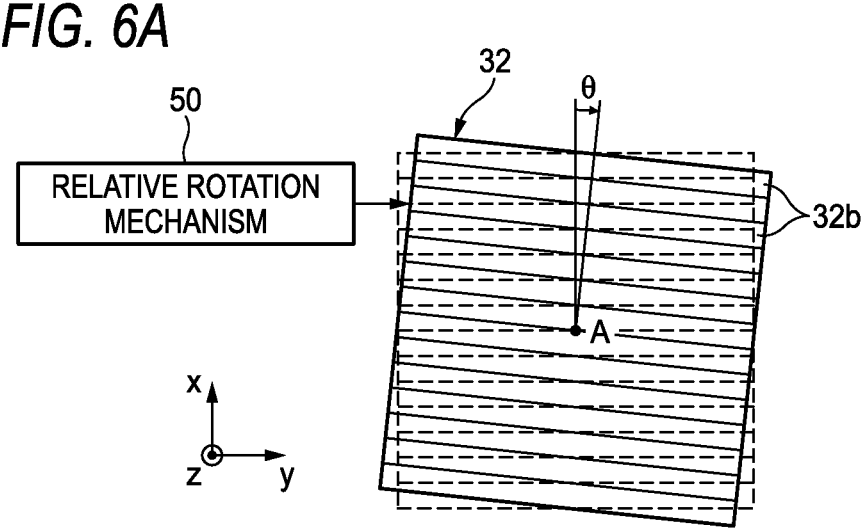
FIGS. 6A to 6C are diagrams schematically illustrating a mechanism for changing the period of moiré fringes due to overlaying of first and second gratings.
Figure 6B:
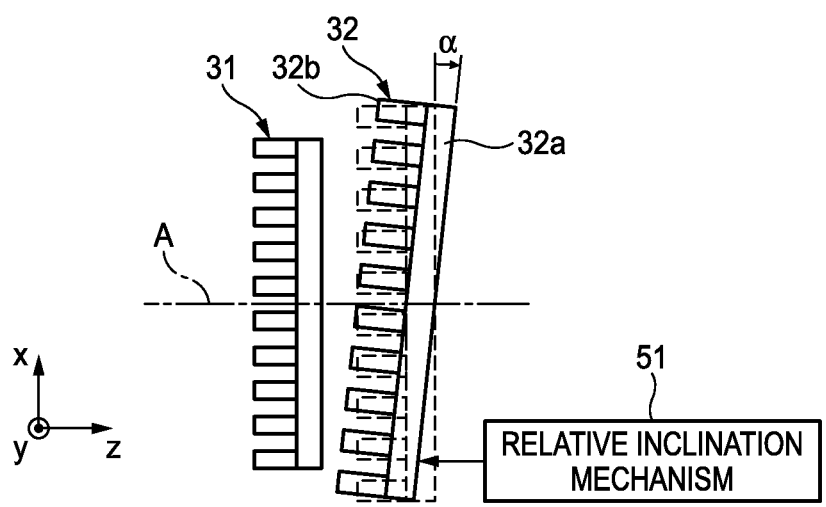
Figure 6C:
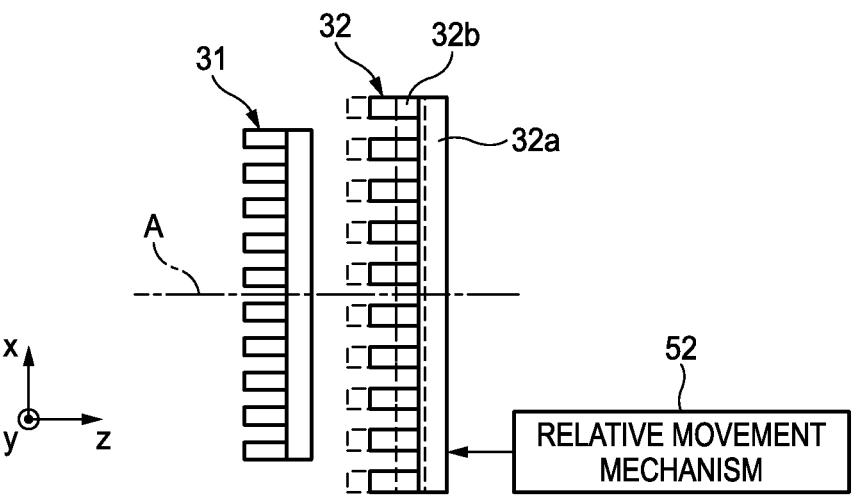

FIGS. 6A, 6B and 6C illustrate methods of changing the moiré period T. It is possible to change the moiré period T by relatively rotating one of the first and second absorption type gratings 31, 32 about the optical axis A. For example, there is provided a relative rotation mechanism 50 that rotates the second absorption type grating 32 relatively to the first absorption type grating 31 about the optical axis A. When the second absorption type grating 32 is rotated by an angle θ by the relative rotation mechanism 50, the substantial grating pitch in the x direction is changed from "$p_2'$" to "$p_2'/\cos \theta$", so that the moiré period T is changed (refer to FIG. 6A).

As another example, it is possible to change the moiré period T by relatively inclining one of the first and second absorption type gratings 31, 32 about an axis orthogonal to the optical axis A and following the y direction. For example, there is provided a relative inclination mechanism 51 that inclines the second absorption type grating 32 relatively to the first absorption type grating 31 about an axis orthogonal to the optical axis A and following the y direction. When the second absorption type grating 32 is inclined by an angle α by the relative inclination mechanism 51, the substantial grating pitch in the x direction is changed from "$p_2'$" to "$p_2' \times \cos \alpha$", so that the moiré period T is changed (refer to FIG. 6B).

As another example, it is possible to change the moiré period T by relatively moving one of the first and second absorption type gratings 31, 32 along a direction of the optical axis A. For example, there is provided a relative movement mechanism 52 that moves the second absorption type grating 32 relatively to the first absorption type grating 31 along a direction of the optical axis A so as to change the distance $L_2$ between the first absorption type grating 31 and the second absorption type grating 32. When the second absorption type grating 32 is moved along the optical axis A by a moving amount δ by the relative movement mechanism 52, the pattern period of the G1 image of the first absorption type grating 31 projected at the position of the second absorption type grating 32 is changed from "$p_1'$" to "$p_1' \times (L_1+L_2+\delta)/(L_1+L_2)$", so that the moiré period T is changed (refer to FIG. 6C).

In the X-ray imaging system 10, since the imaging unit 12 is not the Talbot interferometer and can freely set the distance $L_2$, it can appropriately adopt the mechanism for changing the distance $L_2$ to thus change the moiré period T, such as the relative movement mechanism 52. The changing mechanisms (the relative rotation mechanism 50, the relative inclination mechanism 51 and the relative movement mechanism 52) of the first and second absorption type gratings 31, 32 for changing the moiré period T can be configured by actuators such as piezoelectric devices.

When the subject H is arranged between the X-ray source 11 and the first absorption type grating 31, the moiré fringe that is detected by the FPD 30 is modulated by the subject H. An amount of the modulation is proportional to the angle of the X-ray that is deviated by the refraction effect of the subject H. Accordingly, it is possible to generate the phase contrast image of the subject H by analyzing the moiré fringe detected by the FPD 30.

In the below, an analysis method of the moiré fringe is described.

Figure 7:
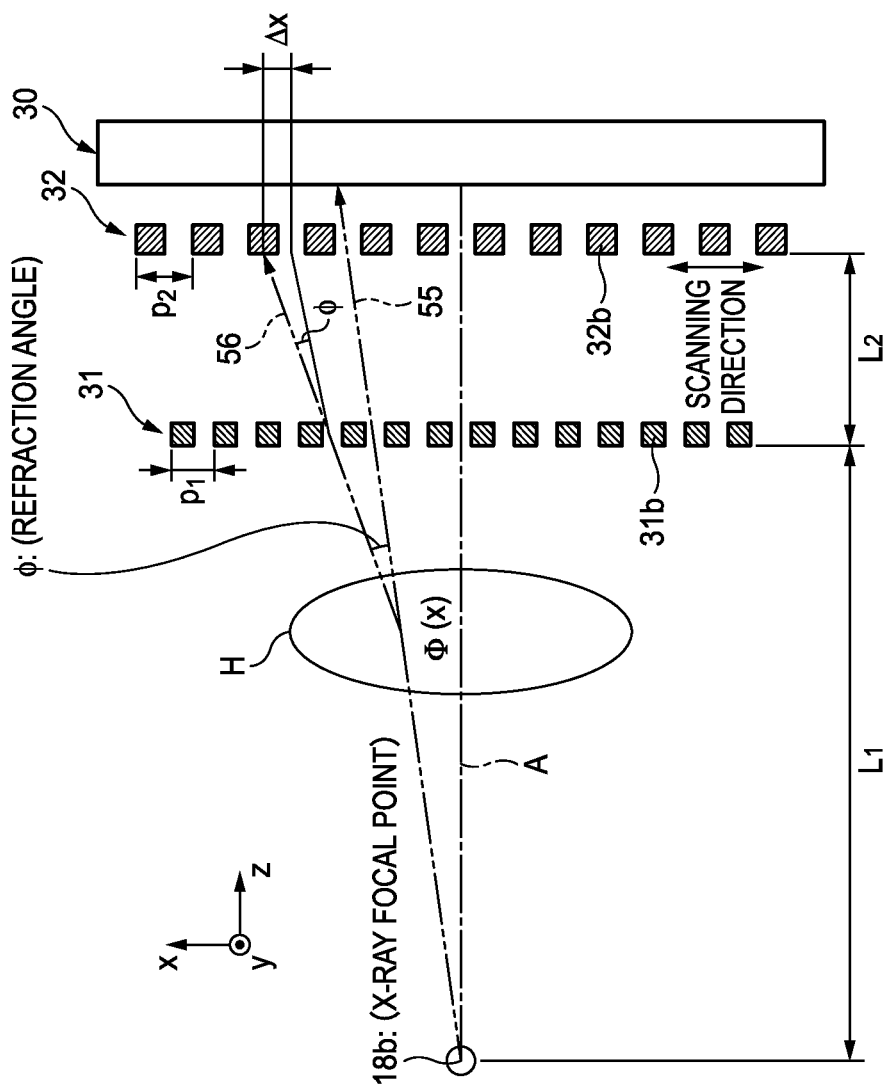
FIG. 7 is a diagram schematically illustrating refraction of radiation due to a subject.

FIG. 7 illustrates one X-ray that is refracted in correspondence to a phase shift distribution $\Phi(x)$ in the x direction of the subject H.

A reference numeral 55 indicates a path of the X-ray that goes straight when there is no subject H. The X-ray traveling along the path 55 passes through the first and second absorption type gratings 31, 32 and is then incident onto the FPD 30. A reference numeral 56 indicates a path of the X-ray that is refracted and deviated by the subject H. The X-ray traveling along the path 56 passes through the first absorption type grating 31 and is then shielded by the second absorption type grating 32.

The phase shift distribution $\Phi(x)$ of the subject H is expressed by a following equation (11), when a refractive index distribution of the subject H is indicated by n(x, z) and the traveling direction of the X-ray is indicated by z.

[equation 11]

$$\Phi(x) = \frac{2\pi}{\lambda} \int [1 - n(x, z)] dz \tag{11}$$

The G1 image that is projected from the first absorption type grating 31 to the position of the second absorption type grating 32 is displaced in the x direction as an amount corresponding to a refraction angle $\phi$, due to the refraction of the X-ray at the subject H. An amount of displacement $\Delta x$ is approximately expressed by a following equation (12), based on the fact that the refraction angle $\phi$ of the X-ray is slight.

[equation 12]

$$\Delta x \approx L_2 \phi \tag{12}$$

Here, the refraction angle $\phi$ is expressed by an equation (13) using a wavelength $\lambda$ of the X-ray and the phase shift distribution $\Phi(x)$ of the subject H.

[equation 13]

$$\varphi = \frac{\lambda}{2\pi} \frac{\partial \Phi(x)}{\partial x} \tag{13}$$

Like this, the amount of displacement $\Delta x$ of the G1 image due to the refraction of the X-ray at the subject H is related to the phase shift distribution $\Phi(x)$ of the subject H. Also, the amount of displacement $\Delta x$ is related to a phase deviation amount $\psi$ of a signal output from each pixel 40 of the FPD 30 (a deviation amount of a phase of a signal of each pixel 40 when there is the subject H and when there is no subject H), as expressed by a following equation (14).

[equation 14]

$$\psi = \frac{2\pi}{p_2} \Delta x = \frac{2\pi}{p_2} L_2 \varphi \tag{14}$$

Therefore, when the phase deviation amount $\psi$ of a signal of each pixel 40 is calculated, the refraction angle $\phi$ is obtained from the equation (14) and a differential of the phase shift distribution $\Phi(x)$ is obtained by using the equation (13). Hence, by integrating the differential with respect to x, it is possible to generate the phase shift distribution $\Phi(x)$ of the subject H, i.e., the phase contrast image of the subject H. In the X-ray imaging system 10 of this illustrative embodiment, the phase deviation amount $\psi$ is calculated by using a fringe scanning method that is described below.

In the fringe scanning method, an imaging is performed while one of the first and second absorption type gratings 31, 32 is stepwise translation-moved relatively to the other in the x direction (that is, an imaging is performed while changing the phases of the grating periods of both gratings). In the X-ray imaging system 10 of this illustrative embodiment, the second absorption type grating 32 is moved by the scanning mechanism 33. However, the first absorption type grating 31 may be moved. As the second absorption type grating 32 is moved, the moiré fringe is moved. When the translation distance (moving amount in the x direction) reaches one period (grating pitch $p_2$) of the grating period of the second absorption type grating 32 (i.e., when the phase change reaches $2\pi$), the moiré fringe returns to its original position. Regarding the change of the moiré fringes, while moving the second absorption type grating 32 by 1/n (n: integer) with respect to the grating pitch $p_2$, the moiré fringes are captured by the FPD 30 and the signals of the respective pixels 40 are obtained from the captured fringe images and calculated in the calculation processing unit 22, so that the phase deviation amount $\psi$ of the signal of each pixel 40 is obtained.

Figure 8:
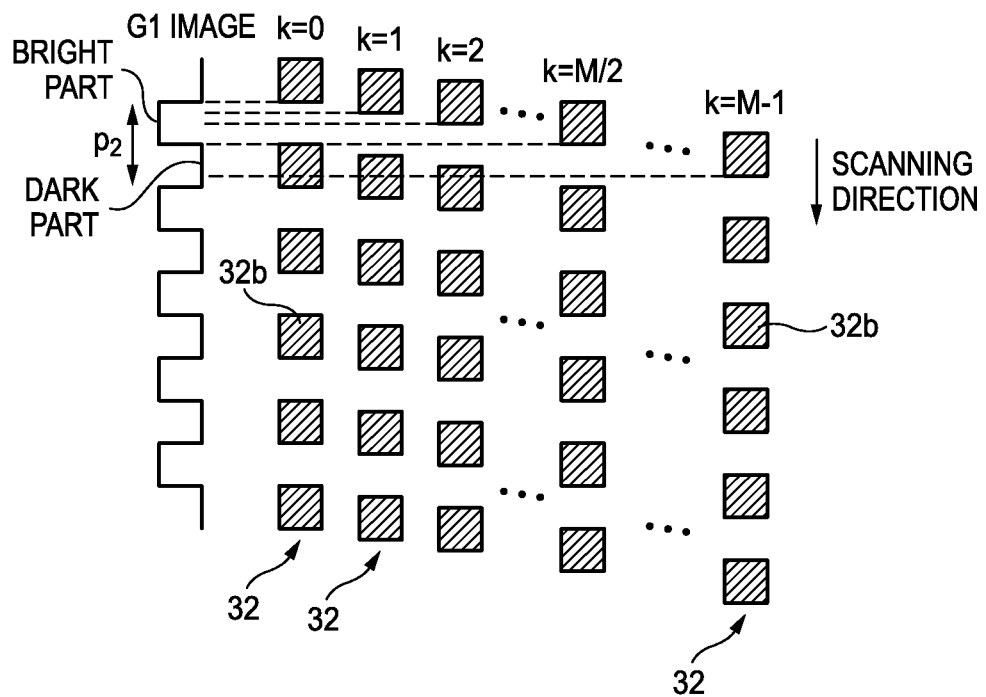
FIG. 8 is a diagram schematically illustrating a fringe scanning method.

FIG. 8 pictorially illustrates that the second absorption type grating 32 is moved with a scanning pitch ($p_2$/M) (M: integer of 2 or larger) that is obtained by dividing the grating pitch $p_2$ into M.

The scanning mechanism 33 sequentially translation-moves the second absorption type grating 32 to each of M scanning positions of k=0, 1, 2, . . . , M−1. In FIG. 8, an initial position of the second absorption type grating 32 is a position (k=0) at which a dark part of the G1 image at the position of the second absorption type grating 32 when there is no subject H substantially coincides with the X-ray shield unit 32b. However, the initial position may be any position of k=0, 1, 2, . . . , M−1.

First, at the position of k=0, mainly, the X-ray that is not refracted by the subject H passes through the second absorption type grating 32. Then, when the second absorption type grating 32 is moved in order of k=1, 2, . . . , regarding the X-ray passing through the second absorption type grating 32, the component of the X-ray that is not refracted by the subject H is decreased and the component of the X-ray that is refracted by the subject H is increased. In particular, at the position of k=M/2, mainly, only the X-ray that is refracted by the subject H passes through the second absorption type grating 32. At the position exceeding k=M/2, contrary to the above, regarding the X-ray passing through the second absorption type grating 32, the component of the X-ray that is refracted by the subject H is decreased and the component of the X-ray that is not refracted by the subject H is increased.

At each position of k=0, 1, 2, ..., M−1, when the imaging is performed by the FPD 30, M signal values (M Pixel data) are obtained for the respective pixels 40. In the below, a method of calculating the phase deviation amount ψ of the signal of each pixel 40 from the M signal values is described. When a signal value of each pixel 40 at the position k of the second absorption type grating 32 is indicated with $I_k(x)$, $I_k(x)$ is expressed by a following equation (15).

[equation 15]

$$I_k(x) = A_0 + \sum_{n>0} A_n \exp\left[2\pi i \frac{n}{p_2}\left\{L_2\varphi(x) + \frac{kp_2}{M}\right\}\right] \quad (15)$$

Here, x is a coordinate of the pixel 40 in the x direction, $A_0$ is the intensity of the incident X-ray and $A_n$ is a value corresponding to the contrast of the signal value of the pixel 40 (n is a positive integer). Also, φ(x) indicates the refraction angle φ as a function of the coordinate x of the pixel 40.

Then, when a following equation (16) is used, the refraction angle φ(x) is expressed by a following equation (17).

[equation 16]

$$\sum_{k=0}^{M-1} \exp\left(-2\pi i \frac{k}{M}\right) = 0 \quad (16)$$

[equation 17]

$$\varphi(x) = \frac{p_2}{2\pi L_2} \arg\left[\sum_{k=0}^{M-1} I_k(x)\exp\left(-2\pi i \frac{k}{M}\right)\right] \quad (17)$$

Here, arg[ ] means the extraction of an angle of deviation and corresponds to the phase deviation amount ψ of the signal of each pixel 40. Therefore, from the M signal values obtained from the respective pixels 40, the phase deviation amount ψ of the signal of each pixel 40 is calculated based on the equation (18), so that the refraction angle φ(x) is acquired.

Figure 9:
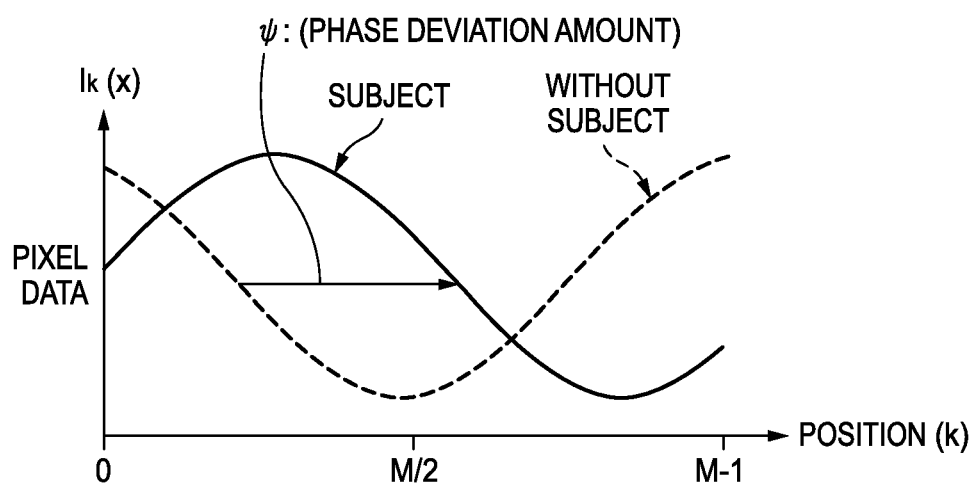
FIG. 9 is a graph illustrating a signal of a pixel of a radiographic image detector in association with the fringe scanning

FIG. 9 illustrates a signal of one pixel of the radiological image detector, which is changed depending on the fringe scanning.

The M signal values obtained from the respective pixels 40 are periodically changed with the period of the grating pitch $p_2$ with respect to the position k of the second absorption type grating 32. The broken line of FIG. 9 indicates the change of the signal value when there is no subject H and the solid line of FIG. 9 indicates the change of the signal value when there is the subject H. A phase difference of both waveforms corresponds to the phase deviation amount ψ of the signal of each pixel 40.

Since the refraction angle φ(x) is a value corresponding to the differential phase value, as shown with the equation (13), the phase shift distribution Φ(x) is obtained by integrating the refraction angle φ(x) along the x axis. In the above descriptions, a y coordinate of the pixel 40 in the y direction is not considered. However, by performing the same calculation for each y coordinate, it is possible to obtain the two-dimensional phase shift distribution Φ(x, y) in the x and y directions.

The above-described calculation is performed by the phase contrast image generating unit 27 of the calculation processing unit 22, and the calculation processing unit 22 stores the calculated phase shift distribution 1 in the image storage unit 23 as a phase contrast image.

Next, an absorption image generation process performed by the absorption image generating unit 28 of the calculation processing unit 22 will be described.

Figure 10:
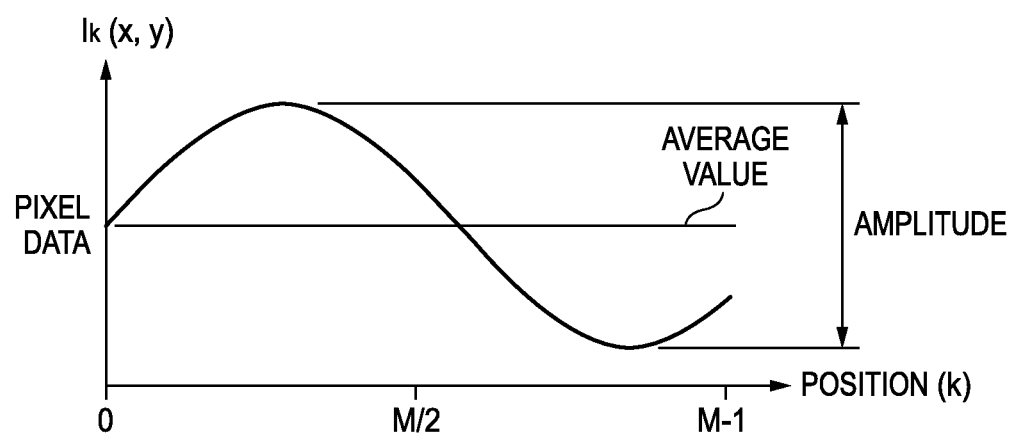
FIG. 10 is a graph illustrating an absorption image generation process in the radiographic system in FIG. 1.

As shown in FIG. 10, the absorption image generating unit 28 averages M signal values $I_k(x, y)$ for each pixel obtained by the above-described fringe scanning with respect to k to calculate an average value, and images the result to generate an absorption image. The calculation of the average value may be performed by simply averaging the signal values $I_k(x, y)$ with respect to k, but an error tends to increase in a case where M is small. Thus, preferably, after the signal values $I_k(x, y)$ are fitted to a sine wave, an average value of the fitted sine wave is calculated.

The absorption image generated by the above-described calculation includes density irregularity due to the fact that the first and second absorption type gratings 31 and 32 are present in an X-ray irradiation field. Thus, the absorption image generating unit 28 performs a shading correction for the absorption image to remove or reduce the density irregularity.

Hereinafter, the shading correction of the absorption image will be described with reference to FIG. 11.

Figure 11:
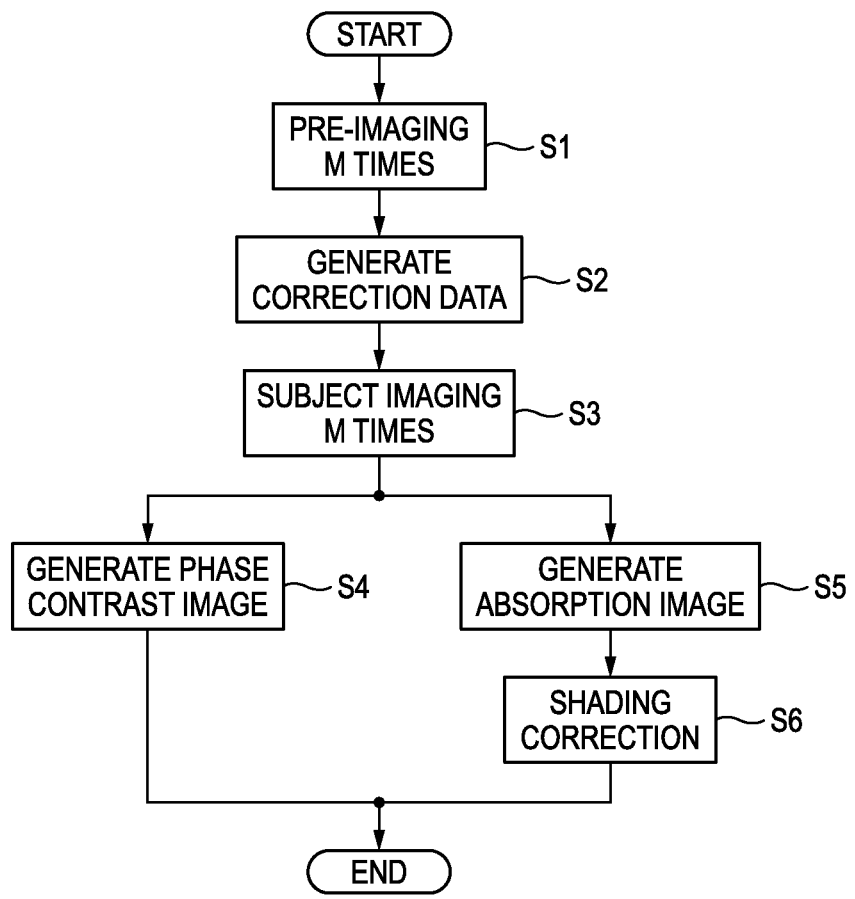
FIG. 11 is a flowchart illustrating a radiographic image generation process in the radiographic system in FIG. 1.

FIG. 11 illustrates the flow of a radiographic image generation process in the radiographic system in FIG. 1.

First, in a state where a subject H is not present, pre-imaging is performed while sequentially translating the second absorption type grating 32 at M respective scanning positions of k=0, 1, 2, ..., M−1 (step S1). Here, a plurality of pieces of image data (hereinafter, referred to as pre-image data) obtained by the FPD 30 is corrected by an offset correction, a gain correction or the like in a correction circuit included in the readout circuit 43, and is transmitted to the calculation processing unit 22.

The calculation processing unit 22 generates shading correction data on the basis of the plurality of pieces of pre-image data (step S2). The correction data is generated by calculating an average value of signal values for each corresponding pixel group between the plurality of pieces of pre-image data. The calculation is the same as in the above-described absorption image generation process, and is performed by the absorption image generating unit 28 of the calculation processing unit 22 in the X-ray imaging system 10. The correction data reflects the density irregularity due to the first and second absorption type gratings 31 and 32.

Then, the subject H is placed, and imaging is performed while sequentially translating the second absorption type grating 32 at the M respective scanning positions of k=0, 1, 2, ..., M−1 under the same radiography conditions (tube voltage, irradiation time and the like) as in the pre-imaging (step S3). Here, a plurality of pieces of image data (hereinafter, referred to as subject image data) obtained by the FPD 30 is corrected by an offset correction, a gain correction or the like in the correction circuit included in the readout circuit 43, and is transmitted to the calculation processing unit 22.

The phase contrast image generating unit 27 of the calculation processing unit 22 calculates the phase shift distribution Φ from the plurality of pieces of subject image data according to the above-described procedure, and stores the result in the image storage unit 23 as a phase contrast image (step S4).

In parallel with the phase contrast image generation process in the phase contrast image generating unit 27, the absorption image generating unit 28 of the calculation processing unit 22 calculates an average value of signal values for each corresponding pixel group between the plurality of pieces of subject image data to generate an absorption image of the subject (step S5).

Further, the absorption image generating unit 28 performs a shading correction of dividing the generated absorption image by the correction data to remove or reduce the density irregularity included in the absorption image (step S6). The calculation processing unit 22 stores the absorption image of the shading-corrected subject in the image storage unit 23.

The fringe scanning, and the phase contrast image generation process and the absorption image generation process are automatically performed as the respective units are operated in a coordinated manner under the control of the control device 20 after imaging is instructed through the input device 21 by an operator, and finally, the phase contrast image and the absorption image of the subject H are overlaid to be displayed on the monitor 24, for example. The display of the phase contrast image and the absorption image on the monitor 24 is performed in an overlaying manner, for example.

As described above, according to the X-ray imaging system 10, since the absorption image is generated from the plurality of pieces of image data obtained for the phase contrast image of the subject, it is possible to achieve a favorable overlaying of the phase contrast image and the absorption image without deviation of an imaging position during imaging of the absorption image, and to reduce the burden of the subject compared with a case where separate imaging is performed for the absorption image. Further, by performing the shading correction for the generated absorption image, it is possible to remove or reduce the density irregularity due to the first and second absorption type gratings 31 and 32 from the absorption image, and to improve the accuracy of diagnosis or inspection.

Further, according to the X-ray imaging system 10, in a case where the subject is present or in a case where the subject is not present, irrespective of reproducibility of the moiré fringes, it is possible to perform the shading correction of the absorption image. That is, even in a radiographic system in the related art, in order to remove or reduce density irregularity due to variation or the like of sensitivity characteristics of each pixel of an FPD, a shading correction is performed in which an absorption image of a subject obtained by imaging the subject is divided by an image obtained when imaging is performed without placing the subject under the same radiography conditions (X-ray tube voltage, X-ray irradiation time, and the like). Here, each of the plurality of images obtained for generating a phase contrast image forms moiré fringes by overlaying a G1 image and a second grating. According to the shading correction in the related art, each subject image data is divided by corresponding pre-image data (pre-image data when the second grating is present at the same scanning position), but in a case where the relative position relationships of the first and second gratings do not match with each other in a case where the subject is present and in a case where the subject is not present, the moiré fringes do not match with each other, and an artifact due to the mismatch of the moiré fringes remains in the image after division. Generally, it is difficult to secure reproducibility of the relative position relationships of the gratings so that the moiré fringes completely match with each other. However, according to the X-ray imaging system 10, the average value of the signal values for each corresponding pixel group between the plurality of pieces of pre-image data is calculated to generate the correction data, and the moiré fringes are removed from the correction data. Thus, it is possible to perform the absorption image shading correction, irrespective of the reproducibility of the moiré fringes.

Also, according to the X-ray imaging system 10, the X-ray is not mostly diffracted at the first absorption type grating 31 and is linearly projected to the second absorption type grating 32. Accordingly, it is not necessary for the irradiated X-ray to have high spatial coherence and thus it is possible to use a general X-ray source that is used in the medical fields, as the X-ray source 11. In the meantime, since it is possible to arbitrarily set the distance $L_2$ from the first absorption type grating 31 to the second absorption type grating 32 and to set the distance $L_2$ to be smaller than the minimum Talbot interference distance of the Talbot interferometer, it is possible to miniaturize the imaging unit 12. Further, in the X-ray imaging system of this illustrative embodiment, since the substantially entire wavelength components of the irradiated X-ray contribute to the projection image (G1 image) from the first absorption type grating 31 and the contrast of the moiré fringe is thus improved, it is possible to improve the detection sensitivity of the phase contrast image and the absorption image.

In the X-ray imaging system 10, a case where the absorption image generated by calculating the average of the signal values for each pixel of the plurality of pieces of subject image data is divided by the correction data to perform the shading correction has been described, but the shading correction may be performed for each of the plurality of piece of subject image data, and the signal values for each pixel of the plurality of pieces of corrected subject image data may be averaged to generate the absorption image. Further, the phase contrast image may be generated on the basis of the plurality of pieces of corrected subject image data.

Further, a case where the X-ray imaging system 10 averages the signal values obtained for each pixel of the absorption image of the plurality of pieces of image data to calculate the average value and generate the absorption image has been described, but in the absorption image generation process, in addition to the average value, an added value obtained by adding up the signal values, or the like may be used as long as it represents an amount corresponding to the average value.

Also, in the X-ray imaging system 10, the refraction angle φ is calculated by performing the fringe scanning for the projection image of the first grating. Thus, it has been described that both the first and second gratings are the absorption type gratings. However, the invention is not limited thereto. As described above, the invention is also useful even when the refraction angle φ is calculated by performing the fringe scanning for the Talbot interference image. Accordingly, the first grating is not limited to the absorption type grating and may be a phase type grating. Also, the analysis method of the moiré fringe that is formed by the superimposition of the X-ray image of the first grating and the second grating is not limited to the above fringe scanning method. For example, a variety of phase restoration methods using the moiré fringe, such as method of using Fourier transform/ inverse Fourier transform known in "J. Opt. Soc. Am. Vol. 72, No. 1 (1982) p. 156", may be also applied.

Also, it has been described that the X-ray imaging system 10 stores or displays, as the phase contrast image, the image based on the phase shift distribution Φ. However, as described above, the phase shift distribution Φ is obtained by integrating the differential of the phase shift distribution Φ obtained from the refraction angle φ, and the refraction angle φ and the differential of the phase shift distribution Φ are also related to the phase change of the X-ray by the subject. Accordingly, the image based on the refraction angle φ and the image based on the differential of the phase shift distribution Φ are also included in the phase contrast image.

Figure 12:
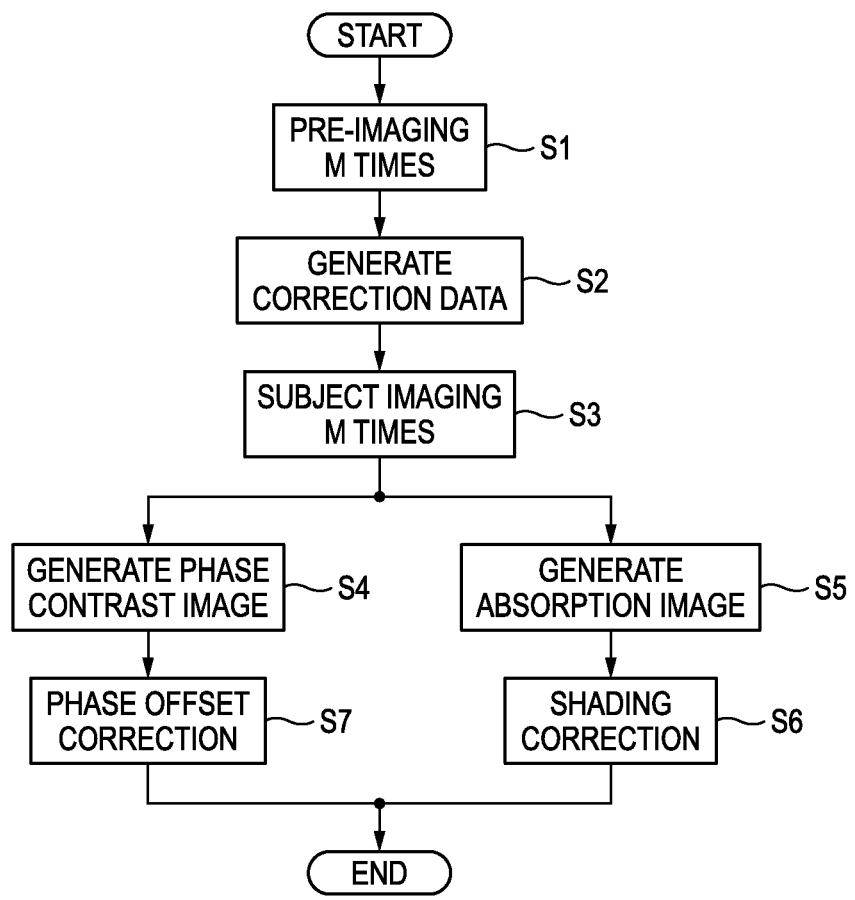
FIG. 12 is a flowchart illustrating a radiographic image generation process with respect to a modified example of the radiographic system in FIG. 1.

FIG. 12 illustrates a radiographic image generation process with respect to a modified example of the radiation photography system in FIG. 1.

In the present modified example, an X-ray phase change (phase offset) due to a factor different from a phase change due to the subject H is corrected. The phase offset may be generated by a pitch error, a scanning error or the like of the first and second absorption type gratings 31 and 32, for example.

The phase contrast image generating unit 27 of the calculation processing unit 22 performs the shading correction for each of the plurality of pieces of pre-image data using the correction data generated in the absorption image generating unit 28, and calculates a phase shift distribution Φ (hereinafter, referred to as a pre-phase shift distribution) according to the above-described procedure on the basis of the plurality of pieces of corrected pre-image data. Further, the phase contrast image generating unit 27 similarly performs the shading correction for each of the plurality of pieces of subject image data, and generates a phase shift distribution Φ (hereinafter, referred to as a subject phase shift distribution) according to the above-described procedure. The pre-phase shift distribution Φ reflects a phase offset due to the pitch error, the scanning error or the like of the first and second absorption type gratings 31 and 32.

Further, the phase contrast image generating unit 27 performs a phase offset correction of subtracting the pre-phase shift distribution Φ from the subject phase shift distribution Φ, to remove or reduce the offset of the phase shift included in the subject phase shift distribution Φ (step S7). The calculation processing unit 22 stores the subject phase shift distribution Φ in which the phase offset is corrected in the image storage unit 23 as a phase contrast image. In this regard, a differential of the pre-shift distribution Φ may be subtracted from a differential of the subject phase shift distribution Φ, and the result may be integrated, to perform the phase offset correction of the subject phase shift distribution Φ.

According to the present modified example, by performing the phase offset correction for the phase contrast image, it is possible to remove or reduce the phase offset due to the pitch error of the first and second absorption type gratings 31 and 32, the scanning error of the first second absorption type grating 32, or the like from the phase contrast image, and to improve the accuracy of diagnosis or inspection.

Figure 13:
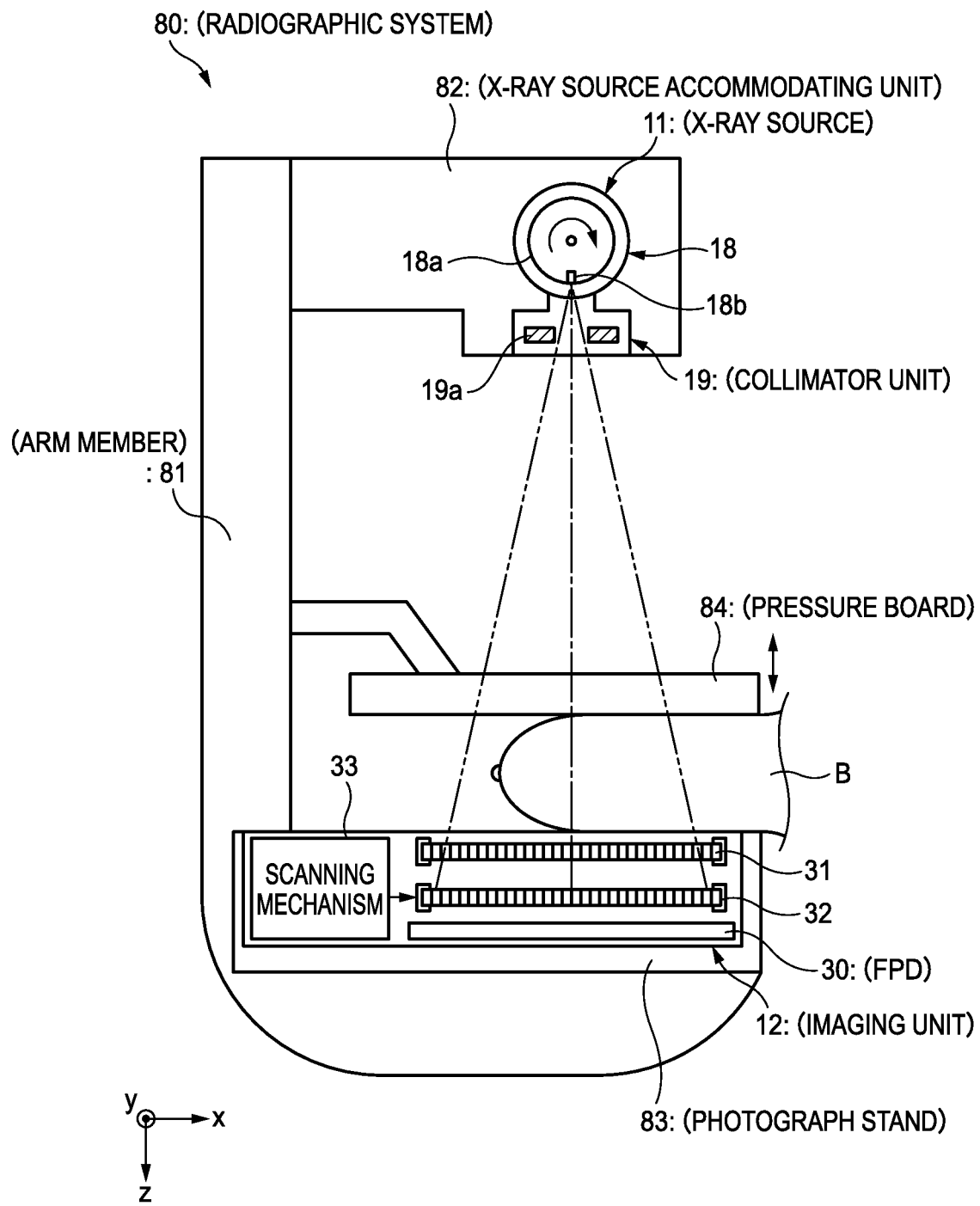
FIG. 13 is a diagram schematically illustrating a configuration of a different example of a radiographic system according to an embodiment of the invention.

FIG. 13 illustrates a different example of a radiographic system according to an embodiment of the invention.

A mammography apparatus 80 shown in FIG. 13 is an apparatus that images an X-ray image (phase contrast image) of a breast B as a subject. The mammography apparatus 80 includes an X-ray source accommodating unit 82 disposed at an end of an arm member 81 that is pivotably connected to a base (not shown), an imaging stand 83 disposed at the other end of the arm member 81, and a pressure board 84 that is provided to be vertically movable with respect to the photograph stand 83.

An X-ray source 11 is accommodated in the X-ray source accommodating unit 82, and an imaging unit 12 is accommodated in the imaging stand 83. The X-ray source 11 and the imaging unit 12 are arranged to face each other. The pressure board 84 moves by a moving mechanism (not shown), and presses the breast B with the breast B being interposed between the pressure board 84 and the imaging stand 83. In this pressed state, the above-described radiography is performed.

Since the X-ray source 11 and the imaging unit 12 have the same configuration as in the above-described X-ray imaging system 10, the same reference numerals as in the X-ray imaging system 10 are given to respective components. Since the other configurations and effects are the same as in the above-described X-ray imaging system 10, description thereof will be omitted.

Figure 14:
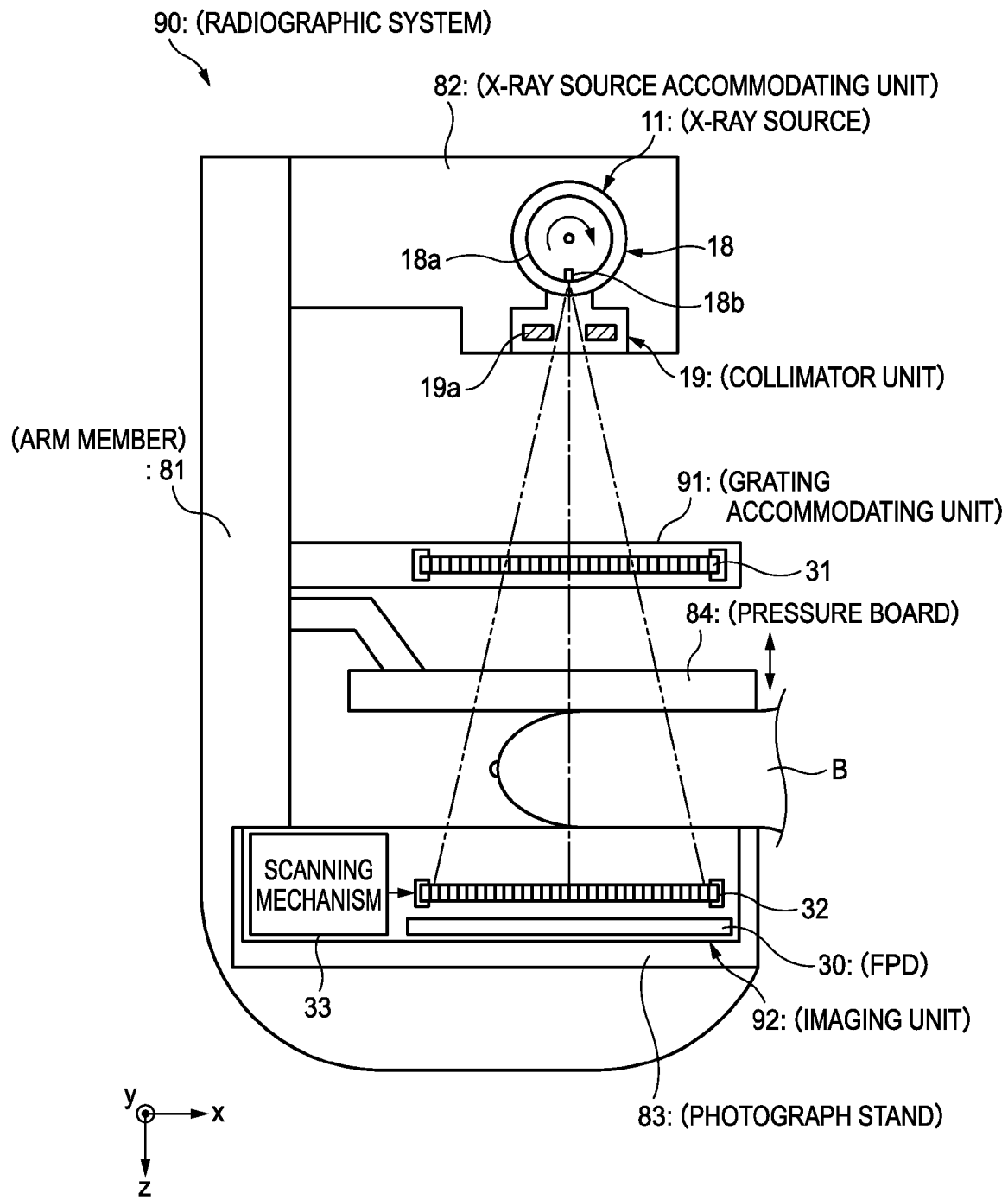
FIG. 14 is a diagram schematically illustrating a configuration of a modified example of the radiographic system in FIG. 13.

FIG. 14 illustrates a modified example of the radiographic system in FIG. 13.

A mammography apparatus 90 shown in FIG. 14 is different from the above-described mammography apparatus 80 in that a first absorption type grating 31 is arranged between the X-ray source 11 and the pressure board 84. The first absorption type grating 31 is accommodated in a grating accommodating unit 91 connected to the arm member 81. An imaging unit 92 includes an FPD 30, a second absorption type grating 32, and a scanning mechanism 33.

In this way, even in a case where the subject (breast) B is disposed between the first absorption type grating 31 and the second absorption type grating 32, a projected image (G1 image) of the first absorption type grating 31 formed at the position of the second absorption type grating 32 is deformed by the subject B. Accordingly, in this case, it is similarly possible to detect moiré fringes modulated due to the subject B by the FPD 30. That is, in the mammography apparatus 90, it is similarly possible to obtain the phase contrast image of the subject B according to the above-described principle.

Further, in the mammography apparatus 90, an X-ray of which the dose is reduced to about a half by shield of the first absorption type grating 31 is irradiated onto the subject B, and thus, it is possible to reduce the exposure dose of the subject B into about a half compared with the case of the mammography apparatus 80. It is possible to apply a configuration in which the subject is disposed between the first absorption type grating 31 and the second absorption type grating 32 such as a mammography apparatus 90 to the above-described X-ray imaging system 10.

Figure 15:
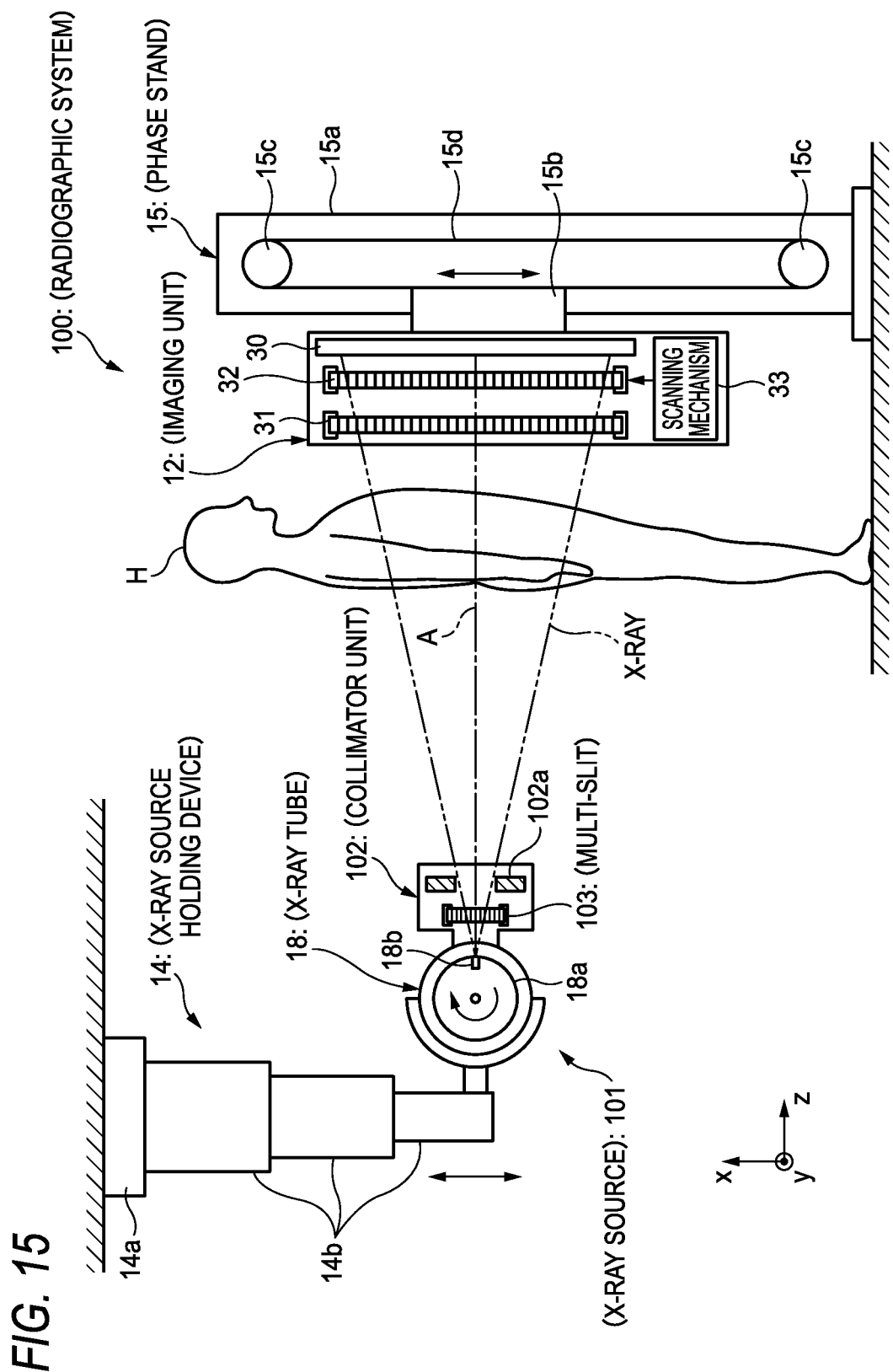
FIG. 15 is a diagram schematically illustrating a configuration of a different example of a radiographic system according to an embodiment of the invention.

FIG. 15 illustrates a different example of a radiographic system according to an embodiment of the invention.

A X-ray imaging system 100 is different from the above-described X-ray imaging system 10 in that a multi-slit 103 is provided in a collimator unit 102 of an X-ray source 101. Since the other configurations are the same as in the above-described X-ray imaging system 10, description thereof will be omitted.

In the above X-ray imaging system 10, when the distance from the X-ray source 11 to the FPD 30 is set to be same as a distance (1 to 2 m) that is set in an imaging room of a typical hospital, the blurring of the G1 image may be influenced by a focus size (in general, about 0.1 mm to 1 mm) of the X-ray focal point 18b, so that the quality of the phase contrast image may be deteriorated. Accordingly, it may be considered that a pin hole is provided just after the X-ray focal point 18b to effectively reduce the focus size. However, when an opening area of the pin hole is decreased so as to reduce the effective focus size, the X-ray intensity is lowered. In the X-ray imaging system 100 of this illustrative embodiment, in order to solve this problem, the multi-slit 103 is arranged just after the X-ray focal point 18b.

The multi-slit 103 is an absorption type grating (i.e., third absorption grating) having the same configuration as the first and second absorption type gratings 31, 32 provided to the imaging unit 12 and has a plurality of X-ray shield units extending in one direction (y direction, in this illustrative embodiment), which are periodically arranged in the same direction (x direction, in this illustrative embodiment) as the X-ray shield units 31b, 32b of the first and second absorption type gratings 31, 32. The multi-slit 103 is to partially shield the radiation emitted from the X-ray source 11, thereby reducing the effective focus size in the x direction and forming a plurality of point light sources (disperse light sources) in the x direction.

It is necessary to set a grating pitch $p_3$ of the multi-slit 103 so that it satisfies a following equation (18), when a distance from the multi-slit 103 to the first absorption type grating 31 is $L_3$.

[equation 18]

$$p_3 = \frac{L_3}{L_2} p_2 \qquad (18)$$

The equation (18) is a geometrical condition so that the projection images (G1 images) of the X-rays, which are emitted from the respective point light sources dispersedly formed by the multi-slit 103, by the first absorption type grating 31 coincide (overlap) at the position of the second absorption type grating 32.

Also, since the position of the multi-slit 103 is substantially the X-ray focus position, the grating pitch $p_2$ of the second absorption type grating 32 is determined to satisfy following equation (19).

[equation 19]

$$p_2 = \frac{L_3 + L_2}{L_3} p_1 \qquad (19)$$

Like this, in the X-ray imaging system 100 of this illustrative embodiment, the G1 images based on the point light sources formed by the multi-slit 103 overlap, so that it is possible to improve the quality of the phase contrast image without lowering the X-ray intensity. The above multi-slit 103 can be applied to any of the X-ray imaging systems.

Figure 16:
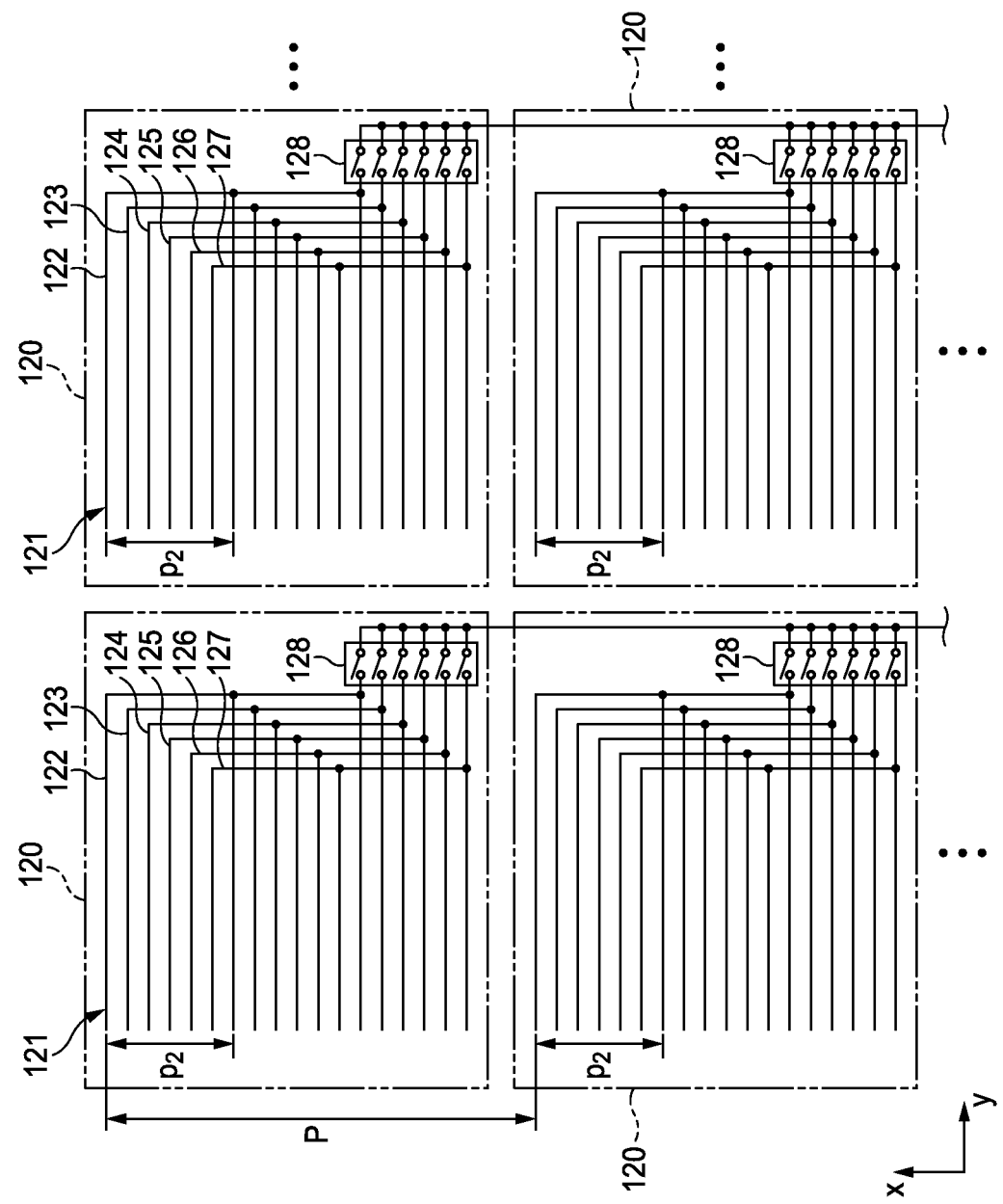
FIG. 16 is a diagram illustrating a configuration of a radiographic image detector with respect to a different example of a radiographic system according to an embodiment of the invention.

FIG. 16 illustrates a configuration of a radiographic image detector with respect to a different example of a radiographic system according to an embodiment of the invention.

In the above-described X-ray imaging system 10, the second absorption type grating 32 is provided independently of the FPD 30, but it is possible to exclude the second absorption type grating by using a radiographic image detector of a configuration disclosed in JP-A-2009-133823. The radiographic image detector is a radiographic image detector of a direct conversion type that includes a conversion layer that converts an X-ray into electric charges and a charge accumulating electrode that accumulates the electric charges converted in the conversion layer, in which a charge accumulating electrode 121 of each pixel 120 is configured by arranging a plurality of wire electrode groups 122 to 127 in which wire electrodes arranged at a constant cycle are electrically connected to each other to have different phases.

The pixels 120 are arranged in a two dimensional manner with a constant pitch along the x direction and the y direction. The charge accumulating electrode 121 for accumulating the electric charges converted by the conversion layer that converts the X-ray into the electrical charges is formed in each pixel 120. The charge accumulating electrode 121 includes the first to sixth wire electrode groups 122 to 127, and an arrangement cycle phase of the wire electrodes of the respective wire electrode groups is deviated by $\pi/3$. Specifically, if the phase of the first wire electrode group 122 is set to 0, the phase of the second wire electrode group 123 is $\pi/3$, the phase of the third wire electrode group 124 is $2\pi/3$, the phase of the fourth wire electrode group 125 is $\pi$, the phase of the fifth wire electrode group 126 is $4\pi/3$, and the phase of the sixth wire electrode group 127 is $5\pi/3$.

The first to sixth wire electrode groups 122 to 127 are formed by periodically arranging the wire electrodes that extend in the y direction at a predetermined pitch p2 in the x direction, respectively. It is necessary that the relationship between a substantial pitch p2' (substantial pitch after manufacturing) of the arrangement pitch p2 of the wire electrodes, a pattern cycle p1' of a G1 image at the position of the charge accumulating electrode 121 (position of the radiographic image detector), and the arrangement pitch P of the pixels 120 in the x direction satisfy Expression (9) on the basis of the cycle T of the moiré fringes expressed as Expression (8), in a similar way to the second absorption type grating 32 of the above-described X-ray imaging system 10, and it is preferable that the relationship satisfy Expression (10).

Further, a switch group 128 for reading the electric charges accumulated by the charge accumulating electrode 121 is provided in each pixel 120. The switch group 128 includes TFT switches that are respectively provided in the first to sixth wire electrode groups 121 to 126. By individually reading the electric charges accumulated by the first to sixth wire electrode groups 121 to 126 by controlling the switch group 128, it is possible to obtain six types of fringe images having different phases by one-time radiography, and to generate a phase contrast image on the basis of the six types of fringe images.

In a case where the radiographic image detector having such a configuration is applied to the above-described X-ray imaging system 10, for example, the second absorption type grating 32 is not necessary from the imaging unit 12. Further, since it is possible to obtain fringe images of a plurality of phase components by one-time radiography, physical scanning for fringe scanning is not necessary, and thus, it is possible to exclude the scanning mechanism 33. Thus, it is possible to reduce the cost and to achieve reduction in thickness of the imaging unit. As the configuration of the charge accumulating electrode, a different configuration disclosed in JP-A-2009-133823 may be used instead of the configuration.

Figure 17:
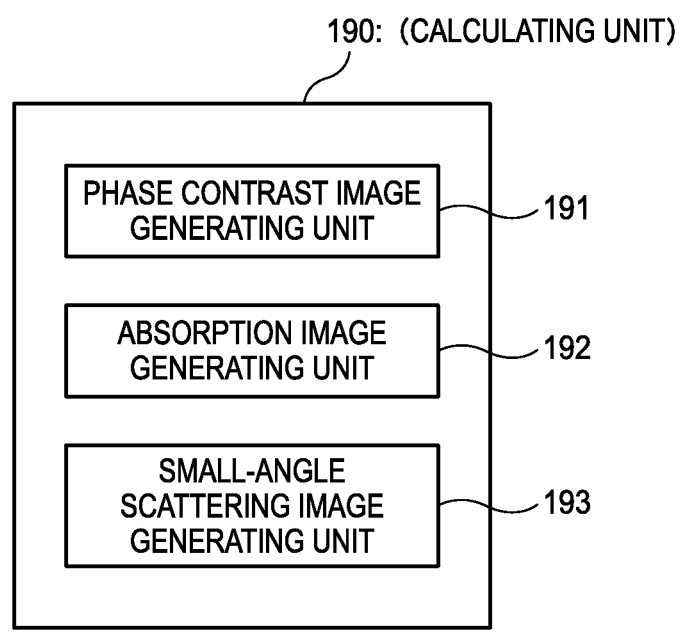
FIG. 17 is a block diagram illustrating a configuration of a radiographic image generating unit with respect to a different example of a radiographic system according to an embodiment of the invention.

FIG. 17 illustrates a configuration of a different example of a radiographic system according to an embodiment of the invention.

In the radiographic system, a calculating unit 190 that is also capable of generating a small-angle scattering image is used. The small-angle scattering image is able to express a tissue characteristic due to a fine structure inside tissue of the subject, and is expected as an expression method for a new image diagnosis in the field of cancer or circulatory diseases, for example. Since the other configurations are the same as in the above-described X-ray imaging system 10, description thereof will be omitted.

The calculating unit 190 includes a phase contrast image generating unit 191, an absorption image generating unit 192, and a small-angle scattering image generating unit 193. All these generating units perform a calculation process on the basis of image data obtained at M scanning positions of k=0, 1, 2, ..., M−1. Here, the phase contrast image generating unit 191 generates a phase contrast image of the subject according to the above-described procedure. Further, the absorption image generating unit 192 generates correction data and an absorption image of the subject according to the above-described procedure.

The small-angle image generating unit 193 generates a small-angle image by calculating an amplitude value of pixel data Ik (x, y) obtained for each pixel for imaging. The calculation of the amplitude value may be performed by calculating a difference between a maximum value and a minimum value of the pixel data Ik (x, y), as shown in FIG. 10, but in a case where M is small, an error increases. Thus, the image data Ik (x, y) is fitted to a sine wave, and then, the amplitude value of the fitted sine wave may be calculated. Further, in generating the small-angle scattering image, it is also possible to use a dispersion value, a standard deviation or the like as an amount corresponding to irregularity around an average value, in addition to the amplitude value.

According to the radiographic system, since the small-angle scattering image is generated from the plurality of images obtained for the phase contrast image of the subject, it is possible to perform favorable overlaying of the phase contrast image or absorption image and the small-angle scattering image without deviation of an imaging position during imaging of the small-angle scattering image, and to reduce the burden of the subject.

In the above-described radiographic system, a case where a general X-ray is used as radiation has been described, but the radiation used in the invention is not limited to the X-ray, and radiation such as an α-ray or a γ-ray other than the X-ray may be used.

As described above, the description discloses a radiographic system including: a first grating; a grating pattern that has a cycle substantially matched with a pattern cycle of a radiographic image formed by radiation that passes through the first grating and is located at a plurality of different relative positions with respect to the radiographic image; a radiographic image detector that detects the radiographic image masked by the grating pattern located at each relative position to obtain a plurality of pieces of image data; a phase contrast image generating unit that generates a phase contrast image on the basis of a plurality of pieces of subject image data obtained by the radiographic image detector when imaging is performed with a subject being placed, in an advancing direction of the radiation that passes through the first grating, in front of the first grating or between the first grating and the grating pattern; and an absorption image generating unit that generates an absorption image on the basis of the plurality of pieces of subject image data, in which the absorption image generating unit performs a shading correction for the absorption image.

The radiographic system disclosed in the description, further includes: a correction data generating unit that generates correction data on the basis of a plurality of pieces of pre-image data obtained by the radiographic image detector when the imaging is performed with the subject being not placed, in which the absorption image generating unit performs the shading correction for the absorption image using the correction data.

In the radiographic system disclosed in the description, the correction data generating unit averages, for each corresponding pixel group between the plurality of pieces of pre-image data, signal values thereof to generate the correction data.

In the radiographic system disclosed in the description, the correction data generating unit adds up, for each corresponding pixel group between the plurality of pieces of pre-image data, signal values thereof to generate the correction data.

In the radiographic system disclosed in the description, the absorption image generating unit averages, for each corresponding pixel group between the plurality of pieces of subject image data, signal values thereof to generate the absorption image.

In the radiographic system disclosed in the description, the absorption image generating unit adds up, for each corresponding pixel group between the plurality of pieces of subject image data, signal values thereof to generate the absorption image.

In the radiographic system disclosed in the description, the phase contrast image generating unit performs the shading correction for the plurality of pieces of subject image data using the correction data, and generates the phase contrast image on the basis of the plurality of pieces of corrected subject image data.

In the radiographic system disclosed in the description, the phase contrast image generating unit performs the shading correction for the plurality of pieces of pre-image data using the correction data, generates a pre-phase contrast image on the basis of the plurality of pieces of corrected pre-image data, and subtracts the pre-phase contrast image from the phase contrast image, to correct the phase contrast image.

In the radiographic system disclosed in the description, the phase contrast image generating unit calculates distribution of a refraction angle of radiation incident onto the radiographic image detector from the plurality of pieces of image data, and generates the phase contrast image on the basis of the distribution of the refraction angle.

Also, the description discloses a radiographic image generating method using a first grating, a grating pattern that has a cycle substantially matched with a pattern cycle of a radiographic image formed by radiation that passes through the first grating and is located at a plurality of different relative positions with respect to the radiographic image, and a radiographic image detector that detects the radiographic image masked by the grating pattern located at each relative position to obtain a plurality of pieces of image data, the method including: performing imaging with a subject being placed, in an advancing direction of the radiation, in front of the first grating or between the first grating and the grating pattern to obtain a plurality of pieces of subject image data; generating a phase contrast image and an absorption image on the basis of the plurality of pieces of obtained subject image data; and performing a shading correction for the generated absorption image.

The radiographic image generating method disclosed in the description, further includes: performing imaging with the subject being not placed to obtain a plurality of pieces of pre-image data; generating correction data on the basis of the plurality of pieces of obtained pre-image data; and performing the shading correction for the absorption image using the generated correction data.

The radiographic image generating method disclosed in the description, further includes: averaging, for each corresponding pixel group between the plurality of pieces of pre-image data, signal values thereof to generate the correction data.

The radiographic image generating method disclosed in the description, further includes: adding up, for each corresponding pixel group between the plurality of pieces of pre-image data, signal values thereof to generate the correction data.

The radiographic image generating method disclosed in the description, further includes: averaging, for each corresponding pixel group between the plurality of pieces of subject image data, signal values thereof to generate the absorption image.

The radiographic image generating method disclosed in the description, further includes: adding up, for each corresponding pixel group between the plurality of pieces of subject image data, signal values thereof to generate the absorption image.

The radiographic image generating method disclosed in the description, further includes: performing the shading correction for the plurality of pieces of subject image data using the correction data, and generating the phase contrast image on the basis of the plurality of pieces of corrected subject image data.

The radiographic image generating method disclosed in the description, further includes: performing the shading correction for the plurality of pieces of pre-image data using the correction data, generating a pre-phase contrast image on the basis of the plurality of pieces of corrected pre-image data, and subtracting the pre-phase contrast image from the phase contrast image, to correct the phase contrast image.

The radiographic image generating method disclosed in the description, further includes: calculating distribution of a refraction angle of radiation incident onto the radiographic image detector from the plurality of pieces of image data, and generating the phase contrast image on the basis of the distribution of the refraction angle.

INDUSTRIAL APPLICABILITY

According to the invention, since the absorption image is generated from the plurality of pieces of image data obtained for the image contrast image, it is possible to perform favorable overlaying of the phase contrast image and the absorption image without deviation of an imaging position during imaging of the absorption image, and to reduce the burden of the subject compared with a case where separate imaging is performed for the absorption image. Further, by performing the shading correction for the generated absorption image, it is possible to remove or reduce density irregularity due to the first grating and the grating pattern from the absorption image, and to improve the accuracy of diagnosis or inspection.

The invention has been described in detail with reference to the specific embodiments, but it is obvious to those skilled in the art that various modifications and changes may be made in a range without departing from the spirit of the invention.

REFERENCE SIGNS LIST

10 RADIOGRAPHIC SYSTEM
11 X-RAY SOURCE
12 IMAGING UNIT
13 CONSOLE
20 CONTROL DEVICE
22 CALCULATION PROCESSING UNIT
27 PHASE CONTRAST IMAGE GENERATING UNIT
28 ABSORPTION IMAGE GENERATING UNIT
30 FPD (RADIOGRAPHIC IMAGE DETECTOR)
31 FIRST ABSORPTION TYPE GRATING (FIRST GRATING)
32 SECOND ABSORPTION TYPE GRATING (GRATING PATTERN)
33 SCANNING MECHANISM
40 PIXEL

The invention claimed is:

1. A radiographic system comprising:
 a first grating;
 a grating pattern that has a cycle substantially matched with a pattern cycle of a radiographic image formed by radiation that passes through the first grating and is located at a plurality of different relative positions with respect to the radiographic image;
 a radiographic image detector that detects the radiographic image masked by the grating pattern located at each relative position to obtain a plurality of pieces of image data;
 a phase contrast image generating unit that generates a phase contrast image on the basis of a plurality of pieces of subject image data obtained by the radiographic image detector when imaging is performed with a subject being placed, in an advancing direction of the radiation that passes through the first grating, in front of the first grating or between the first grating and the grating pattern; and
 an absorption image generating unit that generates an absorption image on the basis of the plurality of pieces of subject image data,
 a correction data generating unit that generates correction data on the basis of a plurality of pieces of pre-image data obtained by the radiographic image detector when the imaging is performed with the subject being not placed,
 wherein the correction data generating unit averages, for each corresponding pixel group between the plurality of pieces of pre-image data, signal values thereof to generate the correction data,
 wherein the absorption image generating unit performs a shading correction for the absorption image using the correction data, and
 wherein the phase contrast image generating unit performs the shading correction for the plurality of pieces of subject image data using the correction data, and generates the phase contrast image on the basis of the plurality of pieces of corrected subject image data.

2. The radiographic system according to claim 1, wherein the absorption image generating unit averages, for each corresponding pixel group between the plurality of pieces of subject image data, signal values thereof to generate the absorption image.

3. The radiographic system according to claim 1, wherein the absorption image generating unit adds up, for each corresponding pixel group between the plurality of pieces of subject image data, signal values thereof to generate the absorption image.

4. The radiographic system according to claim 1, wherein the phase contrast image generating unit performs the shading correction for the plurality of pieces of pre-image data using the correction data, generates a pre-phase contrast image on the basis of the plurality of pieces of corrected pre-image data, and subtracts the pre-phase contrast image from the phase contrast image, to correct the phase contrast image.

5. The radiographic system according to claim 1, wherein the phase contrast image generating unit calculates distribution of a refraction angle of radiation incident onto the radiographic image detector from the plurality of pieces of image data, and generates the phase contrast image on the basis of the distribution of the refraction angle.

6. A radiographic image generating method using a first grating, a grating pattern that has a cycle substantially matched with a pattern cycle of a radiographic image formed by radiation that passes through the first grating and is located at a plurality of different relative positions with respect to the radiographic image, and a radiographic image detector that detects the radiographic image masked by the grating pattern located at each relative position to obtain a plurality of pieces of image data, the method comprising:
 performing imaging with a subject being placed, in an advancing direction of the radiation that passes through the first grating, in front of the first grating or between the first grating and the grating pattern to obtain a plurality of pieces of subject image data;

generating a phase contrast image and an absorption image on the basis of the plurality of pieces of obtained subject image data;

performing imaging with the subject being not placed to obtain a plurality of pieces of pre-image data;

generating correction data on the basis of the plurality of pieces of obtained pre-image data; and performing a shading correction for the generated absorption image using the generated correction data, wherein for each corresponding pixel group between the plurality of pieces of pre-image data, signal values thereof are averaged to generate the correction data;

further comprising: performing the shading correction for the plurality of pieces of subject image data using the correction data, and generating the phase contrast image on the basis of the plurality of pieces of corrected subject image data.

7. The radiographic image generating method according to claim 6, further comprising:

averaging, for each corresponding pixel group between the plurality of pieces of subject image data, signal values thereof to generate the absorption image.

8. The radiographic image generating method according to claim 6, further comprising:

adding up, for each corresponding pixel group between the plurality of pieces of subject image data, signal values thereof to generate the absorption image.

9. The radiographic image generating method according to claim 6, further comprising:

performing the shading correction for the plurality of pieces of pre-image data using the correction data, generating a pre-phase contrast image on the basis of the plurality of pieces of corrected pre-image data, and subtracting the pre-phase contrast image from the phase contrast image, to correct the phase contrast image.

10. The radiographic image generating method according to claim 6, further comprising:

calculating distribution of a refraction angle of radiation incident onto the radiographic image detector from the plurality of pieces of image data, and generating the phase contrast image on the basis of the distribution of the refraction angle.

* * * * *